(12) United States Patent
Osswald et al.

(10) Patent No.: US 9,549,881 B2
(45) Date of Patent: Jan. 24, 2017

(54) STABILIZED DENTAL IMPRESSION COMPOSITION, KIT OF PARTS AND USE THEREOF

(71) Applicant: 3M INNOVATIVE PROPERTIES COMPANY, St. Paul, MN (US)

(72) Inventors: Peter U. Osswald, Tuerkheim (DE); Henning Hoffmann, Windach (DE); Joachim W. Zech, Kaufering (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/767,167

(22) PCT Filed: Feb. 20, 2014

(86) PCT No.: PCT/US2014/017251
§ 371 (c)(1),
(2) Date: Aug. 11, 2015

(87) PCT Pub. No.: WO2014/130603
PCT Pub. Date: Aug. 28, 2014

(65) Prior Publication Data
US 2015/0374591 A1 Dec. 31, 2015

(30) Foreign Application Priority Data
Feb. 25, 2013 (EP) ..................................... 13156549

(51) Int. Cl.
*A61K 6/10* (2006.01)
(52) U.S. Cl.
CPC ....................... *A61K 6/10* (2013.01)
(58) Field of Classification Search
CPC ......... A61K 6/10; A61K 6/0662; A61K 6/093
USPC ....................................................... 523/109
See application file for complete search history.

(56) References Cited

U.S. PATENT DOCUMENTS

| | | |
|---|---|---|
| 3,242,218 A | 3/1966 | Miller |
| 3,661,744 A | 5/1972 | Kehr |
| 3,715,334 A | 2/1973 | Karstedt |
| 3,775,352 A | 11/1973 | Leonard |
| 3,814,730 A | 6/1974 | Karstedt |
| 3,933,880 A | 1/1976 | Bergstrom |
| 4,035,453 A | 7/1977 | Hittmair |
| 4,273,902 A | 6/1981 | Tomioka |
| 4,657,959 A | 4/1987 | Bryan |
| 4,782,101 A | 11/1988 | Waller |
| 5,064,891 A | 11/1991 | Fujiki |
| 5,249,862 A | 10/1993 | Herold |
| 5,286,105 A | 2/1994 | Herold |
| 5,332,122 A | 7/1994 | Herold |
| 5,367,001 A | 11/1994 | Itoh |
| 5,464,131 A | 11/1995 | Keller |
| 5,569,691 A | 10/1996 | Guggenberger |
| 5,677,410 A | 10/1997 | Mager |
| 5,679,755 A | 10/1997 | Mager |
| 5,684,060 A | 11/1997 | Konings |
| 5,750,589 A | 5/1998 | Zech |
| 5,878,907 A | 3/1999 | Graf |
| 5,924,600 A | 7/1999 | Keller |
| 6,135,631 A | 10/2000 | Keller |
| 6,244,740 B1 | 6/2001 | Wagner |
| 6,300,455 B1 | 10/2001 | Haselhorst |
| 6,335,413 B1 | 1/2002 | Zech |
| 6,346,562 B1 | 2/2002 | Haselhorst |
| 6,894,144 B1 | 5/2005 | Zech |
| 7,812,065 B2 | 10/2010 | Bublewitz |
| 8,916,623 B2 | 12/2014 | Riedel |
| 2004/0085854 A1 | 5/2004 | Pauser |
| 2004/0124396 A1 | 7/2004 | Flynn |
| 2005/0027032 A1 | 2/2005 | Hare |
| 2007/0015864 A1 | 1/2007 | Hintzer |
| 2007/0015937 A1 | 1/2007 | Hintzer |
| 2007/0025902 A1 | 2/2007 | Hintzer |
| 2007/0173557 A1 | 7/2007 | Bublewitz |
| 2007/0276068 A1 | 11/2007 | Hintzer |
| 2010/0184881 A1* | 7/2010 | Zech ........................ A61K 6/10 523/109 |

FOREIGN PATENT DOCUMENTS

| | | |
|---|---|---|
| EP | 0188880 | 7/1986 |
| EP | 0231420 | 8/1987 |

(Continued)

OTHER PUBLICATIONS

Van Der Made, "Silane Dendrimers," Journal of the Chemical Society, Chemical Communications, 1992, No. 19, pp. 1400-1401.
Van Der Made, "Dendrimeric Silanes," Advanced Materials, 1993, vol. 5, No. 6, pp. 466-468.
Seyferth, "Synthesis of an Organosilicon Dendrimer Containing 324 Si—H Bonds," Organometallics, 1994, vol. 13, pp. 2682-2690.
Kugel, "Investigation of a New Approach to Measuring Contact Angles for Hydrophilic Impression Materials," Journal of Prosthodontics, Mar.-Apr. 2007, vol. 16, No. 2, pp. 84-92.
International Search report for PCT International Application No. PCT/US2014/017251 mailed on Jul. 7, 2014, 4 pages.

*Primary Examiner* — Tae H Yoon

(57) ABSTRACT

The invention is related to a dental impression composition which is curable at a temperature below about 50 C, the composition comprising: (A) a curable organopolysiloxane polymer as component (A), (B) a crosslinker compound capable of cross-linking said organopolysiloxane polymer as component (B), (C) a catalyst as component (C) capable of catalyzing a crosslinking reaction of component (A) and component (B), (D) a hydrophilizing agent as component (D), (E) a filler as component (E), (F1) a stabilizer as component (F1) selected from compounds comprising a phosphite moiety and mixtures thereof, (F2) a stabilizer as component (F2) selected from antioxidants and mixtures thereof, the composition being present in the form of a base paste and a catalyst paste physically separated from another, the base paste comprising components (A), (B), (D), (E), (F1), (F2), the catalyst paste comprising components (A), (C), (E).

18 Claims, No Drawings

(56) References Cited

FOREIGN PATENT DOCUMENTS

| | | |
|---|---|---|
| EP | 0232733 | 8/1987 |
| EP | 0244478 | 11/1987 |
| EP | 0319639 | 6/1989 |
| EP | 0480238 | 4/1992 |
| EP | 0730913 | 9/1996 |
| EP | 0863088 | 9/1998 |
| EP | 1290998 | 3/2003 |
| EP | 1893163 | 3/2008 |
| EP | 2072029 | 6/2009 |
| EP | 2165693 | 3/2010 |
| EP | 2231102 | 9/2010 |
| WO | WO 98-53791 | 12/1998 |
| WO | WO 99-27895 | 6/1999 |
| WO | WO 2004-060964 | 7/2004 |
| WO | WO 2007-001869 | 1/2007 |
| WO | WO 2007-140091 | 12/2007 |

* cited by examiner

STABILIZED DENTAL IMPRESSION COMPOSITION, KIT OF PARTS AND USE THEREOF

FIELD OF THE INVENTION

The invention relates to a dental impression composition containing stabilizers being suitable to improve the shelf-life of the composition.

BACKGROUND ART

Materials applicable for dental impression are well known in the art.

Commonly used classes of dental impression materials are typically based either on addition- or condensation crosslinking-reactions of polyorganosiloxane containing components as described e.g. in U.S. Pat. No. 5,064,891, EP 0 729 341 A1 or U.S. Pat. No. 4,657,959 or on polyether technology, e.g. azridino-polyethers as described e.g. in EP 1 210 055 B1.

Recently, also hybride materials of polyorganosiloxanes and polyether as described e.g. in EP 1 290 998 A1 are available. The mentioned materials typically possess a variety of properties including a fast setting behaviour and a good dimensional stability. Generally, the materials are provided in two components to be mixed prior to use and cure by a crosslinking-reaction.

An important aspect for dental impression material, especially for polysiloxane based materials (VPS materials), is to make those by nature hydrophobic materials hydrophilic. Means to accomplish this task can be found in EP 1 893 163 A1, EP 2 165 693 A2, EP 0 244 478 B1, EP 0 231 420 B1 or EP 0 613 926 B1. Recently, even improved systems for the hydrophilization of VPS materials have been described, e.g. in EP 1 976 479 B1, EP 2 386 287 A2 or EP 2 231 102 B1.

One problem associated with the higher hydrophilization of silicone impression materials, however, is the storage stability of the obtained pastes, i.e. base paste and catalyst paste.

Therefore, the use of scavengers for the absorption of water such as CaSO4 or CaCl2 as well as Zeolithe A for the stabilization of the base paste have been described in WO 98/53791 A2.

Another approach to stabilize dental impression material is described e.g. in EP 1 893 163 B1 or WO 2007/001869 A2. There, phosphorous based compounds are used for the stabilization of the base paste of hydrophilized addition-curing silicone formulations. U.S. Pat. No. 5,367,001 (Itho et al.) describes an impression composition comprising a polyether polymer having at least two alkenyl groups in the molecule, a polyorganohydrogensiloxane having at least three silicon-bonded hydrogen atoms in its molecule, a platinum catalyst, an inorganic filler and an antioxidant. As suitable fillers fine powdery silica, quartz powder, glass fiber, carbon powder, iron oxide, titanium oxide, zinc oxide, calcium carbonate and magnesium carbonate are described.

WO 99/27895 (Curtis et al.) describes a dental impression composition containing a color change indicator. The impression composition is based on a thermoplastic material like polycaprolactone and may contain filler, an antioxidant and a stabilizer.

US 2007/0173557 A1 (Bublewitz et al.) describes a condensation cross-linked dental material base on alkoxysilyl-functional polyethers. The dental material may contain stabilizers and/or antioxidants.

As nowadays systems with increased hydrophilicity are available, there is a need for improved dental impression materials having e.g. a long shelf-life.

DESCRIPTION OF THE INVENTION

Generally, dental impression compositions should have a shelf life as long as possible in order to be able to store the dental material in higher quantities, without the material losing its characteristic features with regard to material properties before and after curing.

More specifically, there is a need for a curable hydrophilic dental impression composition possessing a good shelf life.

It would also be desirable to have a curable hydrophilic dental impression composition with good shelf life, wherein the formulation of the composition is not limited with respect to the use of certain kind of fillers.

In one embodiment the invention features a dental composition which is curable at a temperature below 50° C., comprising:
(A) a curable organopolysiloxane polymer as component as component (A),
(B) a crosslinker compound capable of crosslinking said organopolysiloxane polymer as component (B),
(C) a catalyst as component (C) capable of catalyzing a crosslinking reaction or component (A) and component (B),
(D) a hydrophilizing agent as component (D),
(E) filler as component (E) comprising cristobalite,
(F1) at least one stabilizer as component (F1) selected from compounds comprising a phosphite moiety and mixtures thereof, preferably

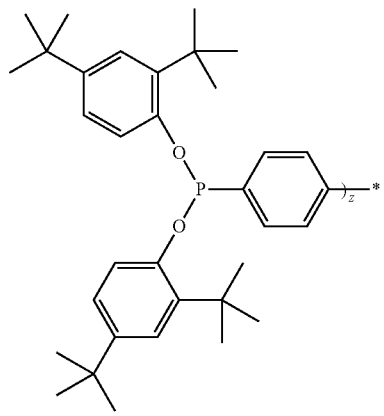

with n = 2

(F2) at least one stabilizer as component (F2) selected from antioxidants and mixtures thereof, preferably pentaerythritoltetrakis(3-(3,5-di-tert-butyl-4-hydroxyphenyl)propionate),
(G) optionally silane compound with only one ethylenically unsaturated group as component (G),
(H) optionally silane compound with at least 2 ethylenically unsaturated groups as component (H),
(I) optionally organopolysiloxanes without unsaturated groups as component (I),
(J) optionally additives as component (J).
the composition being present in the form of a base paste and a catalyst paste physically separated from another, the base paste comprising components (A), (B), (D), (E), (F1), (F2);

the catalyst paste comprising components (A), (C), (E);

and, if present, components (G), (H), (I) and/or (J) being either contained in the base paste or the catalyst paste or the base paste and the catalyst paste.

In another embodiment, the invention relates to a process of producing the dental composition as described in the text of the invention, the process comprising the step of mixing the respective components of the composition.

The invention is also related to a kit of parts and a cartridge containing the components of the inventive composition, the kit of parts comprising a base paste and a catalyst paste. Moreover, the invention features a method of using stabilizer components (F1) and (F2) as described in the present text in combination for increasing the shelf-life of a dental impression composition comprising as filler component (E) cristobalite, especially cristobalite having a pH value of about 4 to about 8 (pH value measurement done on dispersion of 20 g filler in 50 ml of aqueous 0.01N $CaCl_2$ solution, stirred for at least 10 min).

DEFINITIONS

Unless defined differently, for this description the following terms shall have the given meaning: A "dental composition" or a "composition for dental use" or a "composition to be used in the dental field" is any composition which can be used in the dental field.

In this respect the composition should not be detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

The term "compound" is a chemical substance which has a particular molecular identity or is made of a mixture of such substances, e.g., polymeric substances. The term "hydrosilation" means the addition of a compound comprising SiH-groups to a compound containing an aliphatic multiple bond (e.g., an olefinic or acetylenic unsaturation), preferably a vinyl group, —$CH=CH_2$.

By "paste" it is meant a soft, viscous mass of solids dispersed in a liquid. The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

"Sterically hindered phenols" mean chemical components comprising a phenolic moiety with C1-C6 alkyl groups (including iso-proply and ter.-butyl) in the ortho positions of the phenolic moiety. A "hardenable matrix" may be described as the components of a composition contributing to the formation of a network due to chemical interaction (e.g. formation of chemical bondings) between the components thereby leading to a significant change in rheological properties like viscosity.

The terms "vulcanizing, hardening, crosslinking, setting" are used interchangeable and refer to silicones that have as a common attribute the development of a crosslinked elastomer from relatively low molecular weight linear or branched polymers by means of a chemical reaction that simultaneously forms these crosslinks and effectively extends chain length at room temperature.

"Room temperature vulcanizing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is inhibited) at room temperature.

The term "crosslinked polymer," as used herein, refers to polymers that react with the functional group or groups of the polymer chains to lengthen them and connect them, e.g., to form a crosslinked network characteristic of a silicone elastomer. In contrast to a thermoplastic polymer (i.e., a polymer that softens and flows upon heating) a crosslinked polymer, after crosslinking, is characteristically incapable of further flow.

The term "working time" as used herein, refers to the time between the initiation of the setting reaction (e.g., when a vinyl-containing organopolysiloxane, a organohydropolysiloxane, and a platinum catalyst are mixed) and the time the setting reaction has proceeded to the point at which it is no longer practical to perform further physical work upon the system, e.g., reform it, for its intended purpose. When the reaction has proceeded to this later point the material is said to have reached its "gel point." The working time preferably provides enough time to mix and place the composition into its desired form. For many dental impression compositions and applications the working time under conditions of use can be greater than about 30 s (seconds), or greater than about 1 min (minute), or greater than about 2 min. Thus, the working time is typically within a range of about 30 s to about 3 min or about 1 min to about 2 min. So-called "fast-setting" compositions typically have a shorter working time, e.g. less than about 2 min or less than about 1.5 min.

The terms "set time" or "setting time" as used herein, refer to the time at which sufficient curing has occurred so that essentially the material's final cured-state properties are obtained. For a silicone impression material the set time is that time at which one may remove the material from the surface being replicated without causing permanent deformation of the silicone material. The setting time may be approximated, for example, by measuring the torque of the reacting composition on an oscillatory rheometer. When the torque value reaches a maximum value the material is said to be fully set. An arbitrary torque value which is less than the typical maximum value (e.g. 90% of the maximum value) may alternatively be used as a practical approximation of the set time. In general, shorter setting times are preferred over longer setting times. For dental impression compositions the setting time occurs at a time preferably less than about 10 minutes after initiation of the reaction. More preferably the setting time is less than the sum of about 5 minutes plus the working time.

More specifically, the setting time is the time between positioning of the spoon with the dental material in the mouth of the patient and removal of the cured material, and can also be called the mouth residence time or period. Setting times of <about 5 min mouth residence time, preferably <about 4 min, and particularly preferably <about 2 min are desirable properties for the dentist working with impression materials.

For example, the one-phase impression material Imprint™ (3M ESPE) has a setting time of about 5 min, while a typical alginate impression material such as Palgat™ (3M ESPE) has a setting time of about 4 min.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are sodium alginate, agar, polyethers including aziridino substituted polyether materials and silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

"Hydrophilating agents" are agents that are able to either lower the surface tension of water, if used alone (like surfactants), or contribute to a lower surface tension, if used in combination with a surfactant (sometimes referred to as wetting-enabler). If desired, the effect of lowering the surface tension of water can be measured by determining the water-contact angle as described in more detail below.

The term "automixer-suitable impression material" relates to a multi-component impression material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™", "Pentamix™ 2" and "Pentamix™ 3" devices of 3M ESPE Company (cf. U.S. Pat. No. 5,286,105 and U.S. Pat. No. 5,249,862).

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.). Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

One advantage of the invention is that the dental compositions described in the present text have both a relatively high hydrophilicity and show no, or a relatively low level of viscosity increase during extended storage of the compositions.

Thus, if provided in the form of a multi component dental material, like a dental impression material, with a base paste and a catalyst paste wherein at least one of the pastes contains a relatively high amount of surfactant, the component with a high level of surfactant will not prematurely cure during extended storage.

In addition to improved storage stability, the dental composition described in the present text typically also exhibits good tear strength after curing. For example, some of the curable compositions containing organopolysiloxane provide elastomers with good tear strength upon curing and good storage stability as well as sufficient hydrophilicity. This makes them suitable to be used as light body or ultra light body wash materials for taking impressions, especially taking impressions within the oral cavity.

In EP 1 893 163 B1 the stabilizing effect of phosphorous compounds has been demonstrated for base pastes which comprise a comparable low surfactant level (e.g. about 1.5 wt.-% of surfactant with respect to the weight of base paste). Meanwhile, dental impression materials often contain higher amount of surfactant(s).

For these more hydrophilic materials, using phosphorous based stabilizers is not always sufficient to stabilize the base paste. In addition it was found that not only a high amount of hydrophilating agent seems to have an influence on the shelf life of the composition but also the nature of the filler. E.g. it was found that especially cristobalite with a low pH-value (e.g. pH about 4 to about 8, or about 4 to about 7) may have an adverse effect on the shelf life of the base paste.

Surprisingly, it has been found that adding two different kinds of stabilizers—one stabilizer containing a phosphorous atom, the other stabilizer being an antioxidant which preferably contains a phenolic moiety—to the base paste of the curable composition results in improved storage behaviour of the material while the curing behaviour and the material properties remain basically unchanged, even if cristobalite with a low pH-value is used.

Thus, the invention not only facilitates the manufacturing of storage stable dental compositions but also enables the use of fillers having a comparable low pH value during manufacturing. Base pastes containing cristobalite as filler sometimes tend to polymerize even in the absence of a catalyst. By adding an antioxidant to such a base paste the undesired polymerization of the base paste can be prevented.

The dental impression composition described in the present text typically fulfils at least one or more, sometimes all of the following parameters:

Consistency (according to ISO 4823): 0, 1, 2 or 3; and/or

Setting time: within about 15 min after mixing at ambient conditions (e.g. 23° C.).

That is, the curable dental composition can show a comparable low viscous behaviour (type 3), a medium viscosity (type 2), a heavy-bodied consistency (type 1) or a putty-like behaviour (type 0).

According to one embodiment the cured dental composition can be characterized by at least one, more or sometimes all of the following features:

Tensile strength (according to DIN 53504): at least about 0.2 or at least about 2.0 or at least about 3.0 MPa;

Elongation at break (according to DIN 53504): at least about 30%, or at least about 150%, or at least about 200%;

Recovery from deformation (according to ISO 4823): at least about 90%, or at least about 95%, or at least about 98%;

Shore A hardness (according to ISO 4823; 24 h): at least about 20 or at least about 40.

The dental composition can also be characterized by its water contact angle.

Certain embodiments of the composition have a water contact angle of less than about 20° or less than about 13° at a water drop age of 10 s, 60 s after mixing of the components (e.g. determined according to the method described in the Example section below).

Certain embodiments of the composition have alternatively or in addition to the above water contact angle an initial water contact angle of less than about 80°, 40 s after mixing of the components (e.g. determined according to the method described in the Example section below). If desired, the water contact angle can be measured as described in the Example section below.

Component (A) contains one organopolysiloxane or a mixture of two or more polysiloxanes. In the latter case, the "n" polysiloxanes present in component (A) are named (A1), (A2), (An), respectively.

Component (B) contains one organohydrogenpolysiloxane with at least 3 SiH groups per molecule or a mixture of two or more of such organohydrogenpolysiloxanes. In the latter case, the "n" organohydrogenpolysiloxanes present in component (B) can be named (B1), (B2), . . . (Bn), respectively.

Component (C) contains one catalyst capable for catalyzing a crosslinking reaction between component (A) and component (B), Component (D) contains one hydrophilizing agent without reactive substituents or a mixture of two or more of such hydrophilizing agents. In the latter case, the "n" hydrophilizing agents present in component (D) can be named (D1), (D2), . . . (Dn), respectively.

Component (E) contains one filler or a mixture of two or more fillers. In the latter case, the "n" filler present in component (E) can be named (E1), (E2), . . . (En), respectively.

Component (F) contains one stabilizer or a mixture of two or more of such stabilizers. In the latter case, the "n" stabilizers present in component (F) can be named (F1), (F2), . . . (Fn), respectively.

Component (G) is optional. If present, component (G) contains one or more silane compounds with only one ethylenically unsaturated group, or two or more of such compounds. In the latter case, the "n" silane compounds present in component (G) can be named (G1), (G2), . . . (Gn), respectively.

Component (H) is optional. If present, component (H) contains one or more silane compounds with at least 2 ethylenically unsaturated groups or two or more of such compounds. In the latter case, the "n" silane compounds present in component (H) can be named (H1), (H2), . . . (Hn), respectively.

Component (I) is optional. If present, component (I) contains one organopolysiloxanes without reactive substituents or a mixture of two or more of such organopolysiloxanes. In the latter case, the "n" organopolysiloxanes present in component (I) can be named (I1), (I2), . . . (In), respectively.

Component (J) is optional. If present, component (J) contains one or more additives or two or more of such compounds. In the latter case, the "n" additives present in component (J) can be named (J1), (J2), (Jn), respectively.

The dental impression composition contains a curable organopolysiloxane polymer as component (A). The curable organopolysiloxane polymer can also be described as organopolysiloxane with at least two ethylenically unsaturated groups per molecule. The nature and structure of the organopolysiloxane is not particularly limited unless the desired result cannot be achieved.

Component (A) is a curable silicone polymer containing at least two functional groups capable of reacting with a SiH group in the presence of a hydrosilation catalyst. Typically, the curable silicone polymer is an organopolysiloxane with at least two pendant or terminal triorganosiloxy groups in which at least one of the three organic groups is a group with an ethylenically unsaturated double bond.

Generally, the groups with an ethylenically unsaturated double bond can be located on any monomeric unit of the organopolysiloxane. It is, however, preferred, that the groups with an ethylenically unsaturated double bond are located on or at least near the terminal, monomeric units of the polymer chain of the organopolysiloxane. In another embodiment, at least two of the groups with an ethylenically unsaturated double bond are located on the terminal monomeric units of the polymer chain.

The term "monomeric units" relates to repeating structural elements in the polymer that form the polymer backbone, unless expressly stated otherwise.

Preferred organopolysiloxanes can be represented by the following formula:

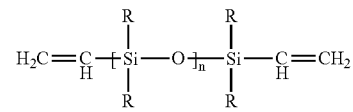

in which the radicals R, independently from each other, represent a non-substituted or substituted, monovalent hydrocarbon group with 1 to about 6 C atoms, which is preferably free from aliphatic multiple bonds and where n generally can be chosen such that the viscosity of the organopolysiloxanes lies between about 1 and about 1,000,000 mPas or between about 2 and about 500,000 or between about 10 and about 100,000 mPas. The parameter n can, e.g., be in the range of about 3 to about 10,000 or from about 10 to about 5,000.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product. The term "detrimental" as used in the context of the present text relates to a change of properties of the precursors or the cured product that negatively affect the usefulness of the precursors or the cured product in their intended use.

In another embodiment of the invention, at least about 50% of the radicals R are methyl groups. Examples of other radicals R that can be present in the organopolysiloxanes according to the above formula are ethyl, propyl, iso-propyl, n-butyl, iso-butyl, tert-butyl, the pentyl isomers, the hexyl isomers, vinyl, allyl, propenyl, iso-propenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is regarded as being part of the disclosure of the present document and is included herein by reference.

The preparation of molecules according to the above-mentioned formula would generally be understood by the skilled person based upon the teachings of the prior art regarding similar molecules.

Particularly preferred are linear polydimethylsiloxanes according to the above formula having viscosities within the specified viscosity ranges and end groups comprising dimethylvinylsiloxy units and methyl groups as the radicals R.

According to another embodiment component (A) can be a QM resin containing vinyl groups.

QM resins comprise as Q a quadrifunctional $SiO_{4/2}$ unit and as M building blocks such as monofunctional units $R_3SiO_{1/2}$, wherein R is vinyl, methyl, ethyl or phenyl or tri- or bi-functional units.

A preferred QM resin which can be used as component (A) has the structure: $Si[O—Si(CH_3)_2—CH=CH_2]_4$. Examples of suitable QM resins are e.g. described in US 2005/0027032. The content of this document with respect to the description of QM resins is herewith incorporated by reference.

QM resins can be used in addition to the organopolysiloxanes described above or instead of the organopolysiloxanes described above.

A component (A) which can be employed can consist of one type (A1) of organopolysiloxane. The organopolysiloxane can have a viscosity starting in the range of about 1 to about 1,000,000 mPas, or about 5 to about 500,000 mPas or about 10 to about 50,000 or about 30 to about 40,000 mPas.

It is, however, also possible that component (A) comprises two or more constituents, (A1), (A2) and so on, which can differ, e.g., in the chemical composition of their backbone, or their molecular weight, or their substituents or their viscosity, or any other differentiating feature or two or more of the above mentioned features.

In one embodiment of the invention the difference in viscosities of different constituents of component (A) can be higher than a factor of 2, e.g., higher than a factor of about 5, higher than a factor of about 10, higher than a factor of about 20, higher than a factor of about 30, higher than a factor of about 40, higher than a factor of about 50, higher than a factor of about 60, higher than a factor of about 70, higher than a factor of about 80, higher than a factor of about 90 or higher than a factor of about 100. The difference in viscosities can be even higher, e.g., higher than a factor of about 200, higher than a factor of about 300, higher than a factor of about 500, higher than a factor of about 800, higher than a factor of about 1,000 or higher than a factor of about 5,000, it should, however, preferably not exceed a value higher than a factor of about 10,000. It should be kept in mind that the values mentioned above relate to a factor for the difference in viscosities, not the viscosity values themselve.

If desired, the viscosity can be measured using a Haake Rotovisco RV20 device (spindle MV, measuring cup NV). The viscosity is typically measured at 23° C. After activation and rectification of the system, spindle MV is installed. Then the material to be measured is filled into the measuring cup NV. Without undue delay, the spindle is lowered into the measuring cup NV. The spindle should be covered by a layer of the material of a maximum thickness of 1 mm. The material to be measured is tempered for 20 min at 23° C. The measurement is started by starting the spindle to turn and the viscosity values (mPas) are recorded starting 20 s after the start of measurement. Care must be exercised to ensure that the measuring cup NV does not rotate or move at any time. A value for the viscosity is obtained in mPas. The above mentioned method of measurement corresponds to DIN 53018-1.

Component (A) can be present in the following amounts:
Lower limit: at least about 10 or at least about 20 wt.-%;
Upper limit: utmost about 55 or utmost about 60 wt.-%;
Range: from about 10 to about 60 or from about 20 to about 55 wt.-%;
wt.-% with respect to the weight of the whole composition.

The dental impression composition also contains a crosslinker compound as component (B) capable of crosslinking said organopolysiloxane polymer. The crosslinker compound is typically an organohydrogenpolysiloxane with at least 3 SiH groups per molecule. The nature and structure of the organohydrogenpolysiloxane is not particularly limited, either unless the desired result cannot be achieved.

By definition, an organohydrogenpolysiloxane does not belong to the group of organopolysiloxanes used as component (A) or part of component (A). An organohydrogenpolysiloxane for use as component (B) typically contains from about 0.01 to about 1.7 wt.-% silicon-bonded hydrogen or from about 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

Organohydrogenpolysiloxanes which can be suitable as component (B) include those having a viscosity of about 10 to about 1,000 mPas or from about 15 to about 550 mPas or from about 20 to about 250 mPas.

Component (B) can be present in the following amounts:
Lower limit: at least about 0.1 or at least about 1 or at least about 3 wt.-%;
Upper limit: utmost about 20 or utmost about 15 or utmost about 10 wt.-%;
Range: from about 0.1 to about 20 or from about 1 to about 15 or from about 3 to about 10 wt.-%;
wt.-% with respect to the weight of the whole composition.

The dental impression composition also contains at least one catalyst as component (C) for promoting the reaction between component (A) and component (B). The nature and structure of the catalyst is not particularly limited, either, unless the desired result cannot be achieved.

This catalyst is typically a platinum catalyst or a platinum containing catalyst, including a platinum complex which can be prepared from hexachloroplatinum acid by reduction with tetramethyldivinyldisiloxane. Such compounds are known to the skilled person.

Any other compounds which catalyze or accelerate addition cross-linking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable. The disclosure of these patents with regard to platinum complexes and their preparation is explicitly mentioned and expressly regarded as part of the disclosure of the present text.

The catalyst component (C) can typically be used in an amount of about 0.00005 to about 0.05 wt.-%, particularly about 0.0002 to about 0.04 wt.-%, calculated as elemental platinum and related to the overall weight of the composition. Components (A), (B) and (C) are constituents of the hardenable matrix of the dental composition.

The dental impression material contains at least one hydrophilizing agent as component (D).

The nature and structure of the hydrophilizing agent is not particularly limited, either, unless the desired result cannot be achieved. As defined above, the term hydrophilizing agent also includes surfactants.

Surfactants or hydrophilizing agents which can be employed can generally be chosen freely from all types of surfactants which improve the hydrophilicity of a silicone moiety containing material (especially, if curable via a hydrosilylation reaction).

Useful surfactants, which can improve the hydrophilicity of a silicone material can generally be chosen from anionic, cationic or non-ionic surfactants or mixtures of two or more of such types of surfactants. It can be preferred, if the dental impression material comprises a non-ionic surfactant as a hydrophilizing agent or a mixture of two or more non-ionic surfactants.

Component (D) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state) over that wetting angle achieved on the same silicon composition without component (D).

In certain embodiments, the surfactant does not contain reactive groups so that it is not incorporated into the polysiloxane network. In certain embodiments the surfactant or at least one of the surfactants, if component (D) comprises two or more surfactants, contains a Si-containing moiety, that is, it can be referred to as a Si-containing surfactant.

Ethoxylated fatty alcohols can be used. Suitable examples are e.g. described in EP 0 480 238 B1. Also preferred are non-ionic surface-active substances including nonylphenolethoxylates, polyethylene glycol-mono- and diesters, sorbitan esters and polyethylene glycol-mono- and diethers. Suitable examples are described e.g. in U.S. Pat. No. 4,782,101. The content of these documents with regard to hydrophilizing agents and their preparation is herewith incorporated by reference.

Suitable hydrophilizing agents also include wetting agents from the group of hydrophilic silicone oils, which are not capable of being covalently incorporated into the hardened polymer network. Suitable hydrophilizing agents are described e.g. in U.S. Pat. No. 4,657,959 and in EP 0 231 420 B1. The content of these documents with regard to hydrophilizing agents and their preparation is herewith incorporated by reference.

Suitable silicone moieties containing surfactants can be summarized under the following formula:

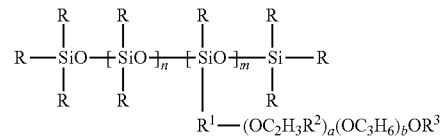

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is about zero or about one, m is about one to about five, a is about five to about 20 and b is about 0.

Several of such ethoxylated surfactants are for example available from Momentive Performance Materials Inc. including "SILWET" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL® SF19, as obtainable from Lubrizol performance products, Spartanburg, US.

Useful surfactants also include polyether carbosilanes of the general formula Q-P—$(OC_nH_{2n})_x$—OT, in which Q stands for $R_3$—Si— or $R_3$—Si—$(R'$—$SiR_2)_a$—R'—$SiR''_2$— where every R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or $R_3SiR'$ in the case of a=0, and a=0-2; P stands for a $C_2$-$C_{18}$ alkylene group, preferably a $C_2$-$C_{14}$ alkylene group or A-R'", where A represents a $C_2$-$C_{18}$ alkylene group and R'" a functional group from the following list: —NHC(O)—, —NHC(O)—(CH$_2$)$_{n-1}$—, —NHC(O)C(O)—, —NHC(O)(CH2)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH2)$_{n-1}$—, —OCH$_2$CH(OH)CH$_2$OC(O)(CH2)$_v$ C(O)— with v=1-12; T is H or stands for a C$_1$-C$_4$ alkyl radical or a C$_1$-C$_4$ acyl radical; x stands for a number from 1 to 200 and n stands for an average number from 1 to 6, preferably 1 to 4. Thus, the element —SiR"$_2$— can also comprise the substructure —Si(R)(R$_3$SiR')—.

The polyether part can be a homopolymer, but can also be a statistical, alternating or block copolymer.

Suitable polyether carbosilanes are selected from the group consisting of: Et$_3$Si—(CH$_2$)$_3$—O—(C$_2$H$_4$ O)y-CH$_3$, Et=Ethyl; Et$_3$Si—CH$_2$—CH$_2$—O—(C$_2$ H$_4$O)y-CH$_3$, Et=Ethyl; (Me$_3$Si—CH$_2$)$_3$Si—(CH$_2$)$_3$—O—(C$_2$H$_4$O)y-CH$_3$, Me=Methyl; Me$_3$Si—CH$_2$—SiMe$_2$-(CH$_2$)$_3$—O—(C$_2$H$_4$O)y-CH$_3$, Me=Methyl; (Me$_3$Si—CH$_2$)$_2$SiMe-(CH$_2$)$_3$—O—(C$_2$H$_4$O)y-CH$_3$, Me=Methyl; Me$_3$Si—(CH$_2$)$_3$—O—(C$_2$H$_4$O)y-CH$_3$, Me=Methyl; Me$_3$Si—CH$_2$—CH$_2$—O—(C$_2$H$_4$O)y-CH$_3$, Me=Methyl; Ph$_3$Si—(CH$_2$)$_3$—O—(C$_2$H$_4$O)y-CH$_3$, Ph=phenyl; Ph$_3$Si—CH$_2$CH$_2$—O—(C$_2$H$_4$O)y-CH$_3$, Ph=phenyl; Cy$_3$Si—(CH$_2$)$_3$—O—(C$_2$H$_4$O)y-CH$_3$, Cy=cyclohexyl; Cy$_3$Si—CH$_2$CH$_2$—O—(C$_2$H$_4$O)y-CH$_3$, Cy=cyclohexyl; (C$_6$H$_{13}$)$_3$Si—(CH$_2$)$_3$—O—(C$_2$H$_4$O)y-CH$_3$, (C$_6$H$_{13}$)$_3$Si—CH$_2$—CH$_2$—O—(C$_4$H$_4$O)y-CH$_3$ in which y conforms to the relation: 5≤y≤20 and mixtures thereof.

Surfactants which can also be used, either alone or as a mixture of two or more thereof, can be found in U.S. Pat. No. 5,750,589 (Zech et al), col. 2, 1.47 to col. 3, 1.27 and col. 3, 1.49 to col. 4, 1.4 and col. 5, 1.7 to col. 14, 1.20.

Other surfactants which can be used, either alone or as a mixture of two or more thereof, can be found in U.S. Pat. No. 4,657,959 (Bryan et al.), col. 4, 1. 46 to col. 6. 1. 52 as well as in EP 0 231 420 B1 (Gribi et al.) p 4, 1. 1 to p. 5, 1. 16 and in the examples.

The content of these documents with regard to hydrophilizing agents and their preparation is herewith incorporated by reference.

In a particular embodiment, a mixture of a silicone moieties containing surfactant and one or more non-ionic surfactants selected from alkoxylated hydrocarbon surfactants is used.

Examples of useful non-ionic surfactants include those according to the formula:

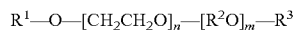

R$^1$—O—[CH$_2$CH$_2$O]$_n$—[R$^2$O]$_m$—R$^3$ wherein R$^1$ represents an aromatic or aliphatic, linear or branched hydrocarbon group having at least 8 carbon atoms, R$^2$ represents an alkylene having 3 carbon atoms, R$^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which R$^1$ in the above formula represents an alkyl group of 4 to 20 carbon atoms, m is 0 and R$^3$ is hydrogen. An example thereof includes isotridecanol ethoxylated with about 8 ethoxy groups and which is commercially available as GENAPOL®X080 from Clariant GmbH. Non-ionic surfactants according to the above formula in which the hydrophilic part comprises a block-copolymer of ethoxy groups and propoxy groups may be used as well. Such non-ionic surfactants are commercially available from Clariant GmbH under the trade designation GENAPOL® PF 40 and GENAPOL® PF 80. Further suitable non-ionic surfactants that are commercially available include Tergitol™ TMN 6, Tergitol™ TMN 10, or Tergitol™ TMN 100x. Also statistical, alternating or block copolymers of ethylene oxide and propylene oxide are suitable surfactants according to the present invention. Such non-ionic surfactants are available e.g. under the trade name Breox A, Synperonic or Pluronic.

Besides or in addition to the hydrophilazing agent(s) described above, the composition may comprise any of the following components:

ethylene oxide or propylene oxide polymers or ethylene-propylene block polymers bearing as end groups polymerizable moieties selected from vinyl, allyl, —OCO—(CH$_3$)C=CH$_2$;

H$_3$C—CO—[CH$_2$—CH$_2$—O—]$_m$[CH$_2$—CH$_2$—CH$_2$—O—]$_n$—CO—CH$_3$ with n,m=10 to 100.

In addition to the hydrophilazing agent(s) mentioned above, the composition may also comprise an one or more F-containing component as hydrophilating agent (component (D)).

Suitable examples of the F-containing compound include:
T$_1$-X—[(O—CF$_2$—CF$_2$)$_n$—(O—CF$_2$)$_v$—(O—CF(CF$_3$)—CF$_2$)$_w$—(O—CF$_2$—CF$_2$—CF$_2$)$_x$—O]—X-T$_2$
with u=0 to 8, v=0 to 8, w=0 to 14 and x=0 to 8 and u+v+w+x≥1, wherein T$_1$ and T$_2$ can be equal or different and are independently selected from the group consisting of —COOR, —CONR$_b$R$_c$, —CH$_2$OH, —CF$_2$OR, —CHFOH, —CHFOR, —CH$_2$OR or —F with R and being a linear or branched alkyl residue (C1 to C9), aryl residue (C1 to C9) or alkylaryl residue (C1 to C9) each of which may optionally be substituted with one or more substituents selected from the group consisting of hydroxyl, amino group, halogen atom, an SiH group and a group capable of reacting with SiH, R$_b$ and R$_c$ independently representing H or having a meaning as given for R, and wherein X is selected from (CF$_2$)$_{1-6}$, CF(CF$_3$) and CHF—CF$_2$.

More precisely, the F-containing component can also be characterized by any of the following formulas:

Rf—(O)$_t$—CHF—(CF$_2$)$_x$-T, with t=0 or 1, x=0 or 1 and Rf being a linear or branched per- or partly fluorinated alkyl residue (including C1 to C6 or C1 to C4), wherein the alkyl chain can be interrupted by O atoms, with the proviso that when t is 0, the Rf group is a linear or branched per- or partly fluorinated alkyl residue (including C1 to C6 or C1 to C4) interrupted by one or more O atoms Rf—(OCF$_2$)$_m$—O—CF$_2$-T, with m=1 to about 6 and Rf being a linear or branched per- or partly fluorinated alkyl residue rest (including C1 to C6 or C1 to C4), wherein the alkyl chain can be interrupted by O atoms, CF$_3$—(CF$_2$)$_2$—(OCF(CF$_3$)—CF$_2$)$_z$—O-L-T, with z=0, 1, 2, 3, 4, 5, 6, 7 or 8, L having a structure selected from —CF(CF$_3$)—, —CF$_2$—, —CF$_2$CF$_2$— and —CHFCF$_2$, Rf—(O—CF$_2$CF$_2$)$_n$—O—CF$_2$-T, with n=1, 2, 3, 4 or 5 and Rf being a linear or branched per- or partly fluorinated alkyl residue (including C1 to C6 or C1 to C4), wherein the alkyl chain can be interrupted by O atoms, an oligomeric compound obtainable by the anionic or photochemical (in the presence of oxygen) polymerization or copolymerisation of monomers selected from vinylidenfluoride, hexafluoropropylenoxide, tetrafluoroethylene, 2,2,3,3-tetrafluorooxetane, trifluoroethylene or monofluoroethylene, wherein at least one chain-end of the oligomeric compound is represented by a function T, T being selected from the group consisting of —COOR, —CONR$_b$R$_c$, —CH$_2$OH, —CF$_2$OR, —CHFOH, —CHFOR, —CH2OR or —F with R and being a linear or branched alkyl residue (C1 to C9), aryl residue rest (C1 to C9) or alkylaryl residue (C1 to C9) each of which may optionally be substituted with one or more substituents selected from the group consisting of hydroxyl, amino group, halogen atom, an SiH group and a group capable of reacting with SiH, Rb and Rc independently representing H or having a meaning as given for R.

Specific examples of T include:

a) homo- or copolymerization of hexafluoropropylenoxide and/or 2,2,3,3-tetrafluorooxetane;

b) homo- or copolymerization of vinylidenfluoride, hexafluoropropylenoxide, tetrafluoroethylene, 2,2,3,3-tetrafluorooxetane, trifluoroethylene and/or monofluoroethylene in the presence of oxygen. In particular, the esters, especially the methylesters, and the amidols (T=C(O)NH-alkyl-OH) and the respective alcohols or methylethers, prepared by chemical reduction, of the following structures can be used.

Specific examples of F-containing compounds, which can be used, include those listed below:

Rf—O—CHF-T, with Rf being a linear or branched per- or partly fluorinated alkyl chain (including C1 to C6), which can be interrupted by oxygen atoms.

Specific examples according to the above formula include:

CF$_3$—O—CF$_2$—O—CF$_2$—CF$_2$—O—CHF-T

CF$_3$—(O—CF$_2$)$_2$—O—CF$_2$—CF$_2$—O—CHF-T

CF$_3$—(O—CF$_2$)$_3$—O—CF$_2$—CF$_2$—O—CHF-T

Rf—O—CHF—CF$_2$-T, with Rf being a linear or branched per- or partly fluorinated alkyl chain (including C1 to C6), which can be interrupted by oxygen atoms.

CF$_3$—O—CF$_2$—O—CF$_2$—CF$_2$—O—CHF—CF$_2$-T

CF$_3$—(O—CF$_2$)$_2$—O—CF$_2$—CF$_2$—O—CHF—CF$_2$-T

CF$_3$—(O—CF$_2$)$_3$—O—CF$_2$—CF$_2$—O—CHF—CF$_2$-T

R$_f$—O—CF$_2$—CHF-T, with Rf being a linear or branched per- or partly fluorinated alkyl chain (including C1 to C6), which can be interrupted by oxygen atoms.

Specific examples according to the above formula include:

C$_3$F$_7$—O—CF$_2$—CHF-T

CF$_3$—O—CF$_2$—O—CF$_2$—CF$_2$—O—CF$_2$—CHF-T

CF$_3$—(O—CF$_2$)$_2$—O—CF$_2$—CF$_2$—O—CF$_2$—CHF-T

CF$_3$—(O—CF$_2$)$_3$—O—CF$_2$—CF$_2$—O—CF$_2$—CHF-T

Rf—O—CF$_2$—CHF—CF$_2$-T, with Rf being a linear or branched per- or partly fluorinated alkyl chain (including C1 to C6), which can be interrupted by oxygen atoms.

Specific examples according to the above formula include:

C$_3$F$_7$—O—CF$_2$—CHF—CF$_2$-T

CF$_3$—O—CF$_2$—CF$_2$—CF$_2$—O—CF$_2$—CHF—CF$_2$-T

CF$_3$—O—CF$_2$—O—CF$_2$—CF$_2$—O—CF$_2$—CHF—CF$_2$-T

CF$_3$—(O—CF$_2$)$_2$—O—CF$_2$—CF$_2$—O—CF$_2$—CHF—CF$_2$-T

CF$_3$—(O—CF$_2$)$_3$—O—CF$_2$—CF$_2$—O—CF$_2$—CHF—CF$_2$-T

R$_f$—O—CF$_2$—CF$_2$-T, with Rf being a linear or branched per- or partly fluorinated alkyl chain (including C1 to C6), which can be interrupted by oxygen atoms, n=1, 2 or 3 and m=0 or 1.

Specific examples according to the above formula include:

CF$_3$—O—CF$_2$—CF$_2$-T

C$_2$F$_5$—O—CF$_2$—CF$_2$-T

C$_3$F$_7$—O—CF$_2$—CF$_2$-T

C$_4$F$_9$—O—CF$_2$—CF$_2$-T

Rf—(O—CF$_2$)$_u$—O—CF$_2$-T, with Rf being a linear or branched per- or partly fluorinated alkyl chain (including C1 to C6), which can be interrupted by oxygen atoms, and u=1, 2, 3, 4, 5 or 6.

Specific examples according to the above formula include:

CF$_3$—(O—CF$_2$)$_3$—O—CF$_2$-T

CF$_3$—(O—CF$_2$)$_5$—O—CF$_2$-T

Rf—(O—CF$_2$—CF$_2$)$_k$—O—CF$_2$-T, with Rf being a linear or branched per- or partly fluorinated alkyl chain (including C1 to C6), which can be interrupted by oxygen atoms and k=1, 2, 3, 4, 5.

C$_2$F$_5$—(O—CF$_2$—CF$_2$)$_1$—O—CF$_2$-T

C$_3$F$_7$—(O—CF$_2$—CF$_2$)$_1$—O—CF$_2$-T

C$_4$F$_9$—(O—CF$_2$—CF$_2$)$_1$—O—CF$_2$-T

C$_2$F$_5$—(O—CF$_2$—CF$_2$)$_2$—O—CF$_2$-T

CF$_3$—(O—CF$_2$—CF$_2$)$_2$—O—CF$_2$-T

C$_3$F$_7$—(O—CF$_2$—CF$_2$)$_2$—O—CF$_2$-T

C$_4$F$_9$—(O—CF$_2$—CF$_2$)$_2$—O—CF$_2$-T

Rf—O—CF$_2$-T, with Rf being a linear or branched per- or partly fluorinated alkyl chain (including C1 to C6), which can be interrupted by oxygen atoms.

Specific examples according to the above formula include:

C$_3$F$_7$—O—CF$_2$-T

CF$_3$—(CF$_2$)$_2$—(O—CF(CF$_3$)—CF$_2$)$_z$—O—CF(CF$_3$)-T with z=0, 1, 2, 3, 4, 5, 6, 7 or 8.

Specific examples according to the above formula include:

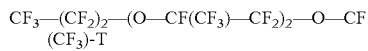

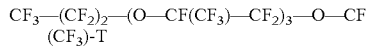

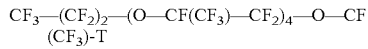

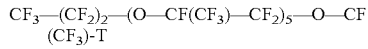

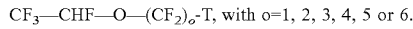

$CF_3$—CHF—O—$(CF_2)_o$-T, with o=1, 2, 3, 4, 5 or 6.

Specific examples according to the above formula include:

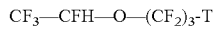

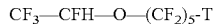

$CF_3$—$CF_2$—O—$(CF_2)_o$-T, with o=1, 2, 3, 4, 5 or 6.

Specific examples according to the above formula include:

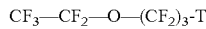

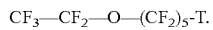

T—$CF_2$—O—$(CF_2—CF_2—O)_p$—$(CF_2—O)_q$—$CF_2$-T, with p/q=about 0.5 to about 3.0 and an molecular weight in the range of about 500 to about 4000 g/mol.

T—$CF_2$—$(OCF(CF_3)CF_2)$ $(OCF_2)_m$—O—$CF_2$-T with n/m=about 20 to about 40 and a molecular weight in the range of about 650 to about 3200 g/mol.

Rf—(O—$CF_2$—$CF_2$—$CF_2)_n$—O—$CF_2$—$CF_2$-T with n=1-25 and Rf being a linear or branched per- or partly fluorinated alkyl chain (including C1 to C6), wherein the alkyl chain can be interrupted by O atoms.

In the above formulas T is selected from the group consisting of —COOR, —CONR$_b$R$_c$, —CH$_2$OH, —CF$_2$OR, —CHFOH, —CHFOR, —CH$_2$OR or —F with R and being a linear or branched alkyl residue (C1 to C9), aryl residue (C1 to C9) or alkylaryl residue (C1 to C9) each of which may optionally be substituted with one or more substituents selected from the group consisting of hydroxyl, amino group, halogen atom, an SiH group and a group capable of reacting with SiH, R$_b$ and R$_c$ independently representing H or having a meaning as given for R.

Suitable fluorinated compounds for use in connection with the present invention include fluorinated polyethers that are commercially available under the tradename FOMBLIN™, GALDEN™ and H-Galden™, Fluorolink™ materials or may be prepared using preparation methods described in US2007/0276068, EP 870877, WO 2004/060964, WO 2007/140091, US 2007/0015864, US 2007/0015864, US 2007/0025902 and US 2007/0015937.

Further examples can be found in EP 2231102 B1. The content of this reference with respect to the description of F-containing components is herewith incorporated by reference.

The F-containing components described above typically function as wetting-enabler, that is, they do not show hydrophiliating properties if used alone (i.e. without an additional surfactant), but increase the hydrophilating properties of an additionally added surfactant.

Particularly useful are hexafluoropropylene oxide (HFPO) derivatives including carboxyl ester derivatives and amidol derivatives of HFPO.

HFPO can be obtained as described in U.S. Pat. No. 3,242,218 or US 2004/0124396. The general formula of a methyl ester derivative of HFPO is $C_3F_7O[CF(CF_3)CF_2O]CF(CF_3)COOCH_3$ with n being 2 to 14.

Component (D) can be present in the following amounts:

Lower limit: at least about 0.1 or at least about 0.75 or at least about 1.5 wt.-%;

Upper limit: utmost about 30 or utmost about 10 or utmost about 5 wt.-%;

Range: from about 0.1 to about 30 or from about 0.75 to about 10 or from about 1.5 to about 5 wt.-%;

wt.-% with respect to the weight of the whole composition.

The composition described in the present text is typically obtained by mixing a base paste and a catalyst paste. In this respect, the hydrophiliating agent can not only be present in the base paste but also in the catalyst paste. In one embodiment of the invention, the hydrophiliating agent is present in the base paste only.

The dental impression material contains filler as component (E). The nature and structure of the filler is not particularly limited, either, unless the desired result cannot be achieved.

A wide variety of inorganic, hydrophilic or hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4-6 μm); amorphous silicone dioxides, such as a diatomaceous earth (4-7 μm); and silanated fumed silica, such as Cab-o-Sil TS-530 (160-240 m$^2$/g), manufactured by Cabot Corporation.

The sizes and surface areas of the foregoing materials can be adjusted to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or alkoxysilanes or silazanes.

Among the fillers which can be used are fillers such as quartz, cristobalite, calcium silicate, diatomaceous earth, zirconium silicate, montmorillonite such as bentonite, zeolite, including molecular sieves such as sodium aluminium silicate, metal oxide powder such as aluminium oxide, titanium oxide or zinc oxide or their mixed oxides, barium sulphate, calcium carbonate, plaster, glass and plastic powder.

Suitable fillers are also pyrogenic or precipitated silicic acid and silica aluminium mixed oxides and metal oxides. Those filler are commercially available from companies like Wacker or Degussa under the trade names Aerosil™, HDK-H or Aeroxide™.

The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 μm.

A combination of reinforcing and non-reinforcing fillers can be preferred. In this respect, the quantity of reinforcing fillers can range from about 0.1 to about 10 wt.-%, in particular from about 0.4 to about 8 wt.-% with respect to the whole composition.

Typical reinforcing fillers include fumed silica, pyrogenic metal oxides, carbon black and the like. They also can be surface treated and can improve mechanical properties like tensile strength or tear strength, of the cured silicone composition.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Preferred non-reinforcing fillers are quartzes, cristobalites and sodium aluminium silicates which can be surface-treated. The surface treatment can generally be carried out with the same methods as described in the case of the strengthening fillers.

Typical non-reinforcing fillers are quartz, precipitated silicas, diatomaceous earth, aluminas, magnesias, titanium dioxide, zirconium silicate, metallic oxides, and the like. These fillers can be surface treated, e.g. silanated, or non surface treated. Typical particle sizes are about 0.2 to about 20 μm.

Besides the chemical composition, the non-reinforcing filler (e.g. cristobalite) can be characterized by the following parameters:

Mean particle size: from about 1 to about 50 or from about 2 to about 20 μm;

pH-value of a dispersion of 20 g filler in 50 ml aqueous 0.01 N CaCl2 solution: about 3 to about 10 or about 4 to about 9.5.

If desired, the mean or average particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

If desired, the pH-value can be determined as follows: 20 g or filler is dispersed (by stirring) in 50 ml of an aqueous 0.01 N CaCl2 solution for at least 10 min and the measurement of the pH value was done 1 hour after end of stirring e.g. by using a pH electrode (e.g. Metrohm™ 808).

Component (E) can be present in the following amounts:

Typically filler can be used in an amount of from of at least about 5 wt.-% or at least about 20 or at least about 30 wt.-% with respect to the whole composition. There is no particular upper limit, however, typically the amount of filler, if present at all, is used in an amount of at most about 80 wt.-% or at most about 70 wt.-% or at most about 60 wt.-% with respect to the whole composition.

Thus, typical ranges for the filler as component (F) include from about 5 to about 80 or from about 20 to about 70 or from about 30 to about 60 wt.-% with respect to the whole composition.

The dental impression composition contains at least one stabilizer as component (F1) being a compound comprising a phosphite moiety.

Component (F1) can generally comprise any type of stabilizer containing at least one phosphorous atom, provided it does not significantly detrimentally impact the properties of the cured composition or its cure rate or any other important properties of the material described in the present text.

The stabilizer can be organic or inorganic or a mixture of organic and inorganic stabilizers can be used as component (F1). The stabilizer can also contain two or more phosphorous atoms. It is particularly preferred if component (F1) comprises an organic stabilizer containing at least one phosphorous atom, and more particularly, an organic stabilizer selected from the group consisting of organo phosphines, organo-phosphites, organo-phosphonites, di(organo-phosphites), di(organo-phosphonites) and combinations thereof.

Also useful as compound (F1) can be organophosphorous compounds of the formula $R^1{}_nP(OR)_{3-n}$ in which n=0, 1, 2 or 3, R=$C_1$-$C_{18}$-alkyl, $C_6$-$C_{30}$-aryl or $C_7$-$C_{31}$-alkylaryl and $R^1$=R or $(CR'_2)_m$ or $(C_6R'_4)_m$ with H=R or OR and m=10.

Especially useful can be, e.g., compounds according to the general formula $P(R)_3$, wherein R can be the same or different and R=$C_1$-$C_{18}$-alkyl, $C_6$-$C_{30}$-aryl, $C_7$-$C_{31}$-alkylaryl, or $OR^1$ with $R^1$=$C_1$-$C_{18}$-alkyl, $C_6$-$C_{30}$-aryl, $C_7$-$C_{31}$-alkylaryl. The radicals R or $R^1$ can be the same or different.

Moreover, representative stabilizers can have the following general formula:

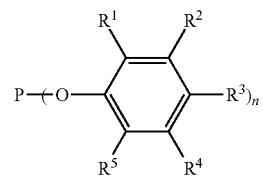

in which $R^1$, $R^2$, $R^3$, $R^4$ and $R^5$ can be the same or different and can be H, saturated or unsaturated, linear or branched C1-C18-alkyl, C6-C30-aryl or C7-C31-alkylaryl and $R^1$, $R^2$, $R^3$, $R^4$ and $R^5$ can optionally be substituted by groups such as amino, mono- or dialkylamino, carboxyl, fluorine, chlorine, bromine, cyano, benzyl, phenyl or toluyl. Compounds which can be used as component E in the context of the invention are disclosed in U.S. Pat. No. 6,300,455 B1 to Haselhorst et al. The disclosure of this document with regard to phosphorous containing compounds and their preparation is incorporated herein by reference and its disclosure is regarded as being part of the disclosure of the present text.

If component F1 is chosen from the compounds according to the formula $R^1{}_nP(OR)_{3-n}$, n can be 0, 1, 2 or 3, R and $R^1$ can independently from each other be:

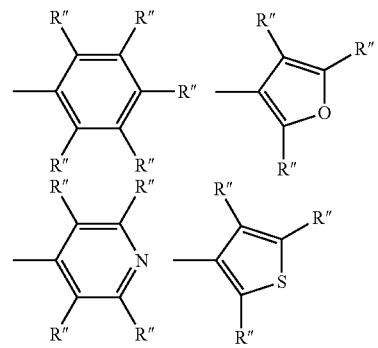

with R" independently from each other being H, $C_1$-$C_{18}$-alkyl, $C_6$-$C_{30}$-aryl or $C_7$-$C_{31}$-alkylaryl, halogen (Hal), $SiR_3$, OR and the like, especially as described in U.S. Pat. No. 6,346,562, the disclosure of this document with regard to phosphorous containing compounds and their preparation is incorporated herein by reference and the disclosure is regarded as being part of the disclosure of the present text.

Also useful as constituents of component (F1) are triphenylphosphite (commercially available as Lankromark® LE65 by Akcros Chemicals), diisodecylphenylphosphite (commercially available as Lankromark® LE76 from Akcros Chemicals or as Hostanox® P-EPQ from Clariant), diphenyl-2-ethylhexylphosphite (commercially available as Lankromark® LE98 from Akcros Chemicals), diphenylisodecylphosphite (commercially available as Lankromark® LE131 from Akcros Chemicals), trisnonylphenylphosphite (commercially available as Lankromark® LE109 from Akcros Chemicals), tris(isodecyl)phosphate (commercially available as Lankromark® LE164 from Akcros Chemicals) or tris(tridecyl)phosphate (commercially available as Lankromark® LE406 from Akcros Chemicals) or mixtures of two or more of these compounds.

Particularly preferred as a constituent of component (F1) is a compound according to the formula:

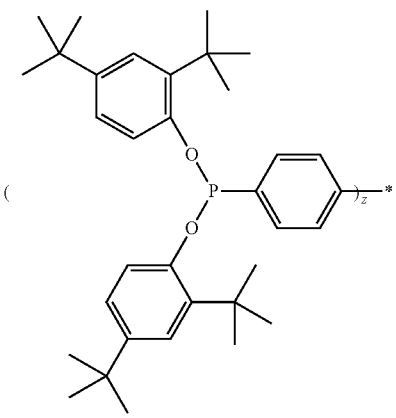

with z=2 (commercially available as Hostanox® P-EPQ from Clariant), Triphenylphosphite (commercially available as Lankromark® LE 65 from Akcros Chemicals) or Diisodecylphenylphosphite (commercially available as Lankromark® LE 76 from Akcros Chemicals).

The amount of component (F1) to be used in the dental composition described in the present text can be within a broad range as long as the desired effect on the storage stability is achieved and side effects with regard to the material properties of the cured material or other properties of the material according to the invention are minor.

Component (F1) can be present in the following amounts:
Lower limit: at least about 0.0001 or at least about 0.0005 or at least about 0.001 wt.-%;
Upper limit: utmost about 0.1 or utmost about 0.07 or utmost about 0.05 wt.-%;
Range: from about 0.0001 to about 0.1 or from about 0.0005 to about 0.07 or from about 0.001 to about 0.05 wt.-%;
wt.-% with respect to the weight of the whole composition.

If the composition is provided as a kit of parts comprising a base part or paste and a catalyst part or paste, component (F1) is typically present in the base part only.

The dental impression material further contains at least one stabilizer as component (F2) selected from antioxidants and mixtures thereof.

Component (F2) can generally comprise any type of stabilizer provided it does not significantly detrimentally impact the properties of the cured composition or its cure rate or any other important properties of the material described in the present text.

Useful antioxidant(s) which can be used include:
Vitamin E; N,N'-di-2-butyl-1,4-p henylene diamine; N,N'-di-2-butyl-1,4-phenylene diamine; 2,6-di-tert-butyl-4-methylphenol; 2,4-dimethyl-6-tert-butylphenol; 2,4-dimethyl-6-tert-butylphenol and 2,6-di-tert-butyl-4-methylphenol; 2,6-di-tert-butylphenol; Pentaerythritoltetrakis(3-(3,5-di-tert-butyl-4-hydroxyphenyl)propionate) (Irganox™ 1010); Octyl-3,5-di-tert-butyl-4-hydroxy-hydrocinnamate; Octadecyl 3-(3,5-di-tert-butyl-4-hydroxyphenyl)propionate; 1,3,5-Trimethyl-2,4,6-tris(3,5-di-tert-butyl-4-hydroxybenzyl)benzene; 2,2',4,4'-Tetrakis-tert-butyl-3,3'-dihydroxybiphenyl; 4,4-Butylidenebis(6-tert-butyl-m-cresol); 4,4'-Isopropyliden-bis-(2-tert-butylphenol); 2,2'-methylenebis(6-nonyl-p-cresol); 1,3,5-tris(3,5-di-tert-butyl-4-hydroxybenzyl-)-1,3,5-triazine-2,4,6(1H,3H,5H)trione; or combinations or mixtures thereof Particularly useful are antioxidants comprising a phenolic moiety, especially a sterically hindered phenolic moiety.

In particular, the following component (F2) was found to be useful:

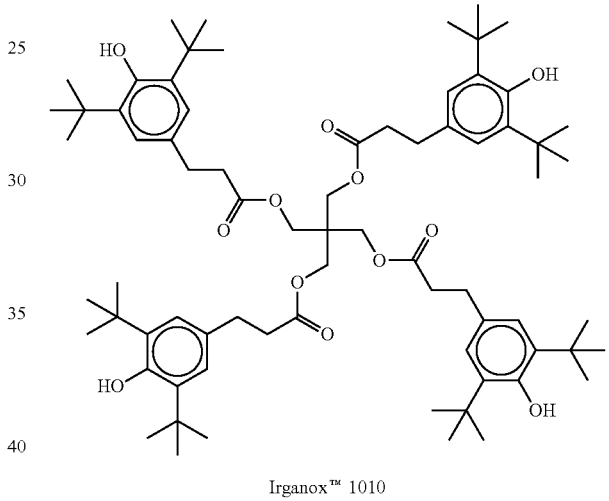

Irganox™ 1010

Component (F2) can be present in the following amounts:
Lower limit: at least about 0.0001 or at least about 0.0005 or at least about 0.001 wt.-%;
Upper limit: utmost about 0.1 or utmost about 0.07 or utmost about 0.05 wt.-%;
Range: from about 0.0001 to about 0.1 or from about 0.0005 to about 0.07 or from about 0.001 to about 0.05 wt.-%;
wt.-% with respect to the weight of the whole composition.

If the composition is provided as a kit of parts comprising a base part and a catalyst part, component (F2) is present in the base part. Component (F2), however, can also be present in the base part and the catalyst part.

The dental composition may also comprise a silane compound with only one ethylenically unsaturated group as optional component (G).

Adding a silane compound with only one ethylenically unsaturated group as component (G) can be beneficial for a number of reasons:

Component (G) might contribute to improve the color stability.

Without wishing to be bound to a particular theory it is assumed that component (G) can absorb hydrogen produced during storage and or use of the composition. Component (G) might also contribute to reducing the setting time.

Without wishing to be bound to a particular theory it is assumed that during the curing reaction component (G) will react with component (A) in an exotherm reaction and thus generating heat, which contributes to an accelerated setting of the curable composition.

Component (G) can typically be characterized by at least one of the following features:
  molecular weight: from about 100 to about 1,000 or from about 200 to about 800 or from about 100 to about 500 or from about 100 to about 300;
  comprising only Si and C containing moieties;
  comprising only one (carbon-carbon) unsaturated silane moiety (e.g. vinyl or allyl);
  not comprising polyether moieties (i.e. at least 3 or 4 or 5 repeating units of ether moieties).

If the molecular weight component (G) is too high, the ability of component (G) to diffuse or migrate within the composition and to interact with other components might be limited. Component (G) can be present in the base paste or the catalyst paste or in the base paste and the catalyst paste.

In some instances it can be advantageous, if component (G) is present in the base paste only.

This can also be beneficial if base paste and catalyst paste are used in a mixing ratio being different from 1:1, especially if the base paste is used in a higher amount (e.g. mixing ratio from base paste to catalyst paste being 2:1 or 5:1 or 10:1). By incorporating component (G) only in the base paste, the overall concentration of component (G) in the mixed composition is increased compared to a composition where component (G) is only in the catalyst paste.

Typical examples for component (G) include components with only one moiety selected from vinyl, allyl, >C=CH—CH$_2$—, >C=C(CH$_3$)—CH$_2$—, vinyl ether and mixtures of either of these components ("<" represents two individual bondings).

Suitable unsaturated silane(s) include those of the following formula:

R2R3C=CR1-A-SiR4

Wherein,

R1, R2, R3 can be equal or different and comprise hydrogen or monovalent alkyl (linear or branched or cycloalkyl) C1-C22, aryl C6-C12 (R1 and R2 or R3 can also combine to a cyclic structure. The residues R1, R2 and R3 may include heteroatoms like O, Cl, Br, F or I. Preferred for R1, R2 and R3 is H.).

R4 can be a monovalent alkyl (linear or branched or cycloalkyl) C1-C22, aryl C6-C12, alkoxy (linear or branched or cycloalkoxy) C1-C22, aryloxy C6-C12, O—SiR53 or H (The residue R may include heteroatoms like O, Cl, Br, F or I. The residues R can be different or equal and are preferably selected from Methyl, Ethyl, Propyl, Isopropyl, Butyl, Isobutyl, sec.-Butyl, tert.-Butyl, Pentyl, Hexyl, Heptyl, Octyl, 2-Ethylhexyl, Nonyl, Decycl, Undecyl, Dodecyl, Tetradecyl, Hexadecyl, Octadecyl Phenyl, Tolyl, Cyclohexyl, Trimethylsiloxy, Triethylsiloxy, tert.-Butyldimethylsiloxy, Methoxy, Ethoxy, Isopropoxy, Butoxy, 3,5,7,9,11,13,15-Heptacyclopentyl-pentacyclo[9.5.13,915, 15.17,13]octasiloxan-1-yl, 3,5,7,9,11,13,15-Heptaisopropyl-pentacyclo[9.5.13,915,15.17,13]octasiloxan-1-yl), R5 can be monovalent alkyl (linear or branched or cycloalkyl) C1-C22, aryl C6-C12, wherein two or three of the residues R4 in O—SiR43 can combine to a cyclic or polycyclic structure like a cyclosiloxane or a polycyclic siloxane structure.

A is a divalent linear, branched or cyclic hydrocarbon group C1-C12, optionally comprising an aromatic moiety, with at least one methylene group directly attached to the unsaturation, optionally including O-Atoms (A is preferably methylene, ethylene, propylene, butylene, hexylene, octylene, nonylene or decyclene).

The unsaturated silane compound comprises preferably the structural element >C=CH—CH$_2$— or >C=C(CH$_3$)—CH$_2$—, preferably the structural element H$_2$C=CH—CH$_2$— or H$_2$C=C(CH$_3$)—CH$_2$—.

Good results can be achieved if the unsaturated silane compound comprises only one allyl group.

Especially preferred are:
H2C=CH—CH2Si(CH3)3; H2C=CH—(CH2)2Si(CH3)3; H2C=CH—(CH2)3Si(CH3)3; H2C=CH—(CH2)4Si(CH3)3; H2C=CH—(CH2)8Si(CH3)3; H2C=CH—CH2Si(i-C3H7)3; H2C=CH—(CH2)2Si(i-C3H7)3; H2C=CH—(CH2)3Si(i-C3H7)3; H2C=CH—(CH2)4Si(i-C3H7)3; H2C=CH—(CH2)8Si(i-C3H7)3; H2C=CH—CH2Si(CH3)2(t-C4H9); H2C=CH—(CH2)2Si(CH3)2(t-C4H9); H2C=CH—(CH2)3Si(CH3)2(t-C4H9); H2C=CH—(CH2)4Si(CH3)2(t-C4H9); H2C=CH—(CH2)8Si(CH3)2(t-C4H9); H2C=CH—CH2Si(C2H5)3; H2C=CH—(CH2)2Si(C2H5)3; H2C=CH—(CH2)3Si(C2H5)3; H2C=CH—(CH2)4Si(C2H5)3; H2C=CH—(CH2)8Si(C2H5)3; H2C=CH—CH2Si(CH3)2(n-C18H37); H2C=CH—(CH2)2Si(CH3)2(n-C18H37); H2C=CH—(CH2)3 Si(CH3)2(n-C18H37); H2C=CH—(CH2)4Si(CH3)2(n-C18H37); H2C=CH—(CH2)8 Si(CH3)2(n-C18H37); H2C=CH—CH2Si(CH3)2(C6H5); H2C=CH—(CH2)2Si(CH3)2(C6H5); H2C=CH—(CH2)3Si(CH3)2(C6H5); H2C=CH—(CH2)4Si(CH3)2(C6H5); H2C=CH—(CH2)8Si(CH3)2(C6H5); H2C=CH—CH2-O—Si(CH3)3;H2C=CH—CH2-O—Si(C2H5)3; H2C=CH—CH2-O—Si(i-C3H7)3; H2C=CH—CH2-O—Si(CH3)2(t-C4H9); H2C=CH—CH2-O—Si(CH3)2(n-C18H37); H2C=CH—CH2-O—Si(CH3)2(C6H5); H2C=CH—CH2Si(CH3)2-O—Si(CH3)3; H2C=CH—(CH2)2Si(CH3)2-O—Si(CH3)3; H2C=CH—(CH2)3Si(CH3)2-O—Si(CH3)3; H2C=CH—(CH2)4Si(CH3)2-O—Si(CH3)3; H2C=CH—(CH2)8Si(CH3)2-O—Si(CH3)3; H2C=CH—CH2Si(CH3)(—O—Si(CH3)3)2; H2C=CH—(CH2)2Si(CH3)(—O—Si(CH3)3)2; H2C=CH—(CH2)3Si(CH3)(—O—Si(CH3)3)2; H2C=CH—(CH2)4Si(CH3)(—O—Si(CH3)3)2; H2C=CH—(CH2)8Si(CH3)(—O—Si(CH3)3)2; H2C=CH—CH2Si(—O—Si(CH3)3)3; H2C=CH—(CH2)2Si(—O—Si(CH3)3)3; H2C=CH—(CH2)3Si(—O—Si(CH3)3)3; H2C=CH—(CH2)4Si(—O—Si(CH3)3)3; H2C=CH—(CH2)8Si(—O—Si(CH3)3)3; H2C=CH—CH2Si(OCH3)3; H2C=CH—(CH2)2Si(OCH3)3; H2C=CH—(CH2)3 Si(OCH3)3; H2C=CH—(CH2)4Si(OCH3)3; H2C=CH—(CH2)8Si(OCH3)3; H2C=CH—CH2Si(OC2H5)3; H2C=CH—(CH2)2Si(OC2H5)3; H2C=CH—(CH2)3Si(OC2H5)3; H2C=CH—(CH2)4Si(OC2H5)3; H2C=CH—(CH2)8Si(OC2H5)3; H2C=CH—CH2Si(C6H5)3; H2C=CH—(CH2)2Si(C6H5)3; H2C=CH—(CH2)3Si(C6H5)3; H2C=CH—(CH2)4Si(C6H5)3; H2C=CH—(CH2)8Si(C6H5)3; H2C=C(CH3)-CH2Si(CH3)3; H2C=CH—CH2Si(p-C6H4OCH3); H2C=CH—CH2Si(CH3)2H; H2C=CH—(CH2)2Si(CH3)2H; H2C=CH—(CH2)3Si(CH3)2H; H2C=CH—(CH2)4Si(CH3)2H; H2C=CH—(CH2)8Si(CH3)2H; and mixtures thereof.

Component (G) can be present in the following amounts:
  Lower limit: at least about 0 or at least about 0.2 or at least about 0.4 wt.-%;

Upper limit: utmost about 20 or utmost about 15 or utmost about 10 wt.-%;

Range: from about 0 to about 20 or from about 0.2 to about 15 or from about 0.4 to about 10 wt.-%;

wt.-% with respect to the weight of the whole composition.

According to another embodiment, the material described in the present text can also optionally contain silane compound(s) with at least 2 ethylenically unsaturated groups as a component (H). Adding a silane compound with at least 2 ethylenically unsaturated group as component (H) can be beneficial for a number of reasons:

Component (H) might contribute to improve the tear strength. Component (H) might contribute to adjust the hardness.

Preferred silane compounds follow the general formula:

$$Si(R^1)_n(R^2)_{4-n}.$$

wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms and n is 2, 3 or 4. Especially preferred radicals $R^1$ are vinyl, allyl and propargyl, especially preferred radicals $R^2$ are linear or branched $C_1$-$C_{12}$ alkyl groups. An example for a silane compound which can be used according to the present invention is tetraallylsilane, which corresponds to the above formula when $R^1$ is equal to an allyl radical and n is equal to 4.

Further preferred silane compounds follow the general formula:

$$(R^1)_m(R^2)_{3-m}Si-A-Si-(R^1)(R^2)_3,$$

wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms, a is a bivalent linear or branched or alicyclic, heterocyclic, aromatic or heteroaromatic group with 1 to about 10000 carbon atoms which can contain nitrogen or oxygen atoms and m is 2 or 3, preferably 3. Examples for bivalent radicals A are ethylene, propylene, butylene, penylene, hexylene, heptylene, octylene, nonylene, decylene, —$H_2C$—Ar—$CH_2$—, —$C_2H_4$—Ar—$C_2H_4$— with Ar being an aromatic bivalent radical, preferably phenyl, or bivalent polyether radicals of the general type —$CH_2CH_2CH_2$—O—[$C_aH_{2a}O$]$_b$—$CH_2CH_2CH_2$— with 1≤a≤5 and 0≤b≤2000.

Also suitable as component H are silane dendrimers. Generally, three-dimensional, highly-ordered oligomer and polymer compounds are described as dendrimers, which are synthesized starting from small core molecules by a constantly repeating sequence of reactions. Monomer or polymer molecules with at least one reactive site are suitable as a core molecule. This is converted in a uni- or multi-level reaction with a reactant which accumulates at the reactive site of the core molecule and for its part has two new reactive sites. The conversion of core molecule and reactant yields the core cell (generation zero). By repeating the reaction, the reactive sites in the first reactant layer are converted with further reactants, again at least two new branching sites being introduced into the molecule each time (1$^{st}$ generation).

The progressive branching leads to a geometrical growth of the number of atoms for each generation. As the overall size can only grow linearly because of the number of possible covalent bonds specified by the reactants, the molecules become more tightly packed from generation to generation and they change their shape from starfish-shaped to spherical. Dendrimers of the zero and each further generation can be dendrimers used as component H according to the invention. Preferred are those of the first generation although those of much higher generations can be used.

Dendrimers of the first or higher generations are obtained as a core molecule by conversion of tri- or tetraalkenyl silanes (preferably allyl and vinyl) in a first step with hydrogenchloro-silanes. These products are converted in a further step with alkenyl-Grignard compounds.

Particularly preferred in this case are dendrimers of the first generation of the following formula:

$$SiR^2_x((CH_2)_n-Si-((CH_2)_m-CH=CH_2)_3)_{4-x}.$$

in which $R^2$ is defined as above, n=2, 3, 4 or 5, m=0, 1, 2 or 3, and x=0 or 1.

Particularly preferred dendrimers according to this general formula are: Me-Si(($CH_2$—$CH_2$—Si(vinyl)$_3$)$_3$; Si(($CH_2$—$CH_2$—Si(vinyl)$_3$)$_4$; Me-Si(($CH_2$—$CH_2$—$CH_2$—Si(allyl)$_3$)$_3$; Si(($CH_2$—$CH_2$—$CH_2$—Si(allyl)$_3$)$_4$; Me-Si(($CH_2$—$CH_2$—Si(allyl)$_3$)$_3$; Si(($CH_2$—$CH_2$—Si(allyl)$_3$)$_4$; Me-Si(($CH_2$—$CH_2$—$CH_2$—Si(vinyl)$_3$)$_3$; Si(($CH_2$—$CH_2$—$CH_2$—Si(vinyl)$_3$)$_4$.

A. W. van der Made and P. W. N. M. van Leeuwen describe the main synthesis of those silane dendrimers in J. Chem. Soc. Commen (1992), page 1400 and in Adv. Mater. (1993), 5, no. 6, pages 366 ff. The Synthesis begins for example with complete allylation of tetrachlorosilane to tetraallylsilane using 10% excess of allyl magnesium bromide in diethyl ether. In addition, the allyl groups are hydrosilylized with trichlorosilane in the presence of a platinum catalyst.

Finally, the conversion takes place with allyl magnesium bromide in diethyl ether. As a result, a dendrimer is obtained with 12 allyl end groups. This first generation can also be converted to a second generation, 36 allyl groups being obtained. The Same topic is also dealt with by D. Seyferth and D. Y Son in Organometallics (1994), 13, 2682-2690.

Conversion products of tri- or tetra- or penta- or hexa- or hepta- or octaalkenyl(cyclo)siloxanes with hydrogenchloro-silanes are furthermore possible as a core molecule. These are converted in a further step with alkenyl-Grignard compounds and lead to dendrimers with cyclical or linear siloxane cores.

Both purified tri-, tetra-, penta-, hexa-, hepta- or octasiloxane dendrimers as well as any mixtures of those dendrimers can be used according to the Invention.

Silane dendrimers, the preparation and use as varnishes of which are known from DE 196 03 242 A1 and DE 195 17 838 A1 as well as from EP 0 743 313 A1. Dendrimers listed there are also suitable for the purpose according to the invention. Polyfunctional alkenyl compounds are furthermore suitable as cores.

Particularly suitable are trimethylolpropanetriallylether, tetrallylpentaerythrite, Santolink XI-100 (Monsanto), tetraallyloxyethane, 1,3,5-benzoltricarbonic acid triallyl ester, 1,2,4-benzoltricarbonic acid triallylester, 1,2,4,5-benzoltetracarbonic acid tetrallylester, triallyl phosphate, triallyl citrate, triallyl isocyanurate, triallyloxytriazine, hexaallylinosite, as well as general compounds which possess at least two ethylenically unsaturated groups which can be optionally substituted, for example O-allyl, N-allyl, O-vinyl, N-vinyl or p-vinylphenolether groups.

Possible polyenes are also described in U.S. Pat. No. 3,661,744 and EP 0 188 880 A1. The polyene can have e.g. the following structure: (Y)—(X)m, m being an integer greater than or equal to 2, preferably 2, 3 or 4, and X being chosen from the —[RCR]$_f$, —CR=CRR, —O—CR=CR—R, —S—CR=CR—R, —NR—CR=CR—R group, f being an integer from 1 to 9 and the R radicals having the meanings H, F, Cl, furyl, thienyl, pyridyl, phenyl and substituted phenyl, benzyl and substituted benzyl, alkyl and substituted alkyl, alkoxy and substituted alkoxy as well as cycloalkyl and substituted cycloalkyl and each being able to be the same or different. (Y) is an at least difunctional organic radical which is constructed from atoms which are chosen from the C, O, N, Cl, Br, F, P, Si and H group.

The allyl- and/or vinyl esters of the at least difunctional carbonic acids are for example very suitable polyene compounds. Suitable carbonic acids for this are those with carbon chains of 2 to 20 C atoms, preferably 5 to 15 C atoms. Allyl or vinyl esters of aromatic dicarbonic acids such as phthalic acid or trimellithic acid are also very suitable. Allyl ethers of polyfunctional alcohols, preferably at least trifunctional alcohols are also suitable. Allyl ethers of trimethyl propane, pentaerythrite triallyl ether or 2,2-bisoxyphenyl-propane-bis-(diallyl phosphate) can be named as examples. Compounds of the cyanuric acid triallylester, triallyl triazintrione type and similar are also suitable.

Dendrimers of the above mentioned type and their preparation are described in U.S. Pat. No. 6,335,413 B1. The disclosure of this document with regard to such dendrimers and their preparation is herewith incorporated as reference.

Component (H) can be present in the following amounts:
Lower limit: at least about 0 or at least about 0.001 or at least about 0.01 wt.-%;
Upper limit: utmost about 20 or utmost about 10 or utmost about 5 wt.-%;
Range: from about 0 to about 20 or from about 0.001 to about 10 or from about 0.01 to about 5 wt.-%;
wt.-% with respect to the weight of the whole composition.

According to another embodiment, the curable dental composition of the invention may contain organopolysiloxanes without unsaturated moieties as component (I). Adding a organopolysiloxanes without unsaturated moieties as component (I) can be beneficial for the following reason:

Component (I) might be useful for adjusting the rheological properties.

Polydimethylsiloxanes with trimethylsiloxy end groups are particularly preferred as a constituent of component (I).

Component (I) can be present in the following amounts:
Lower limit: at least about 0 or at least about 0.1 or at least about 0.5 wt.-%;
Upper limit: utmost about 40 or utmost about 30 or utmost about 20 wt.-%;
Range: from about 0 to about 40 or from about 0.1 to about 30 or from about 0.5 to about 20 wt.-%;
wt.-% with respect to the weight of the whole composition.

According to a further embodiment, the composition can also contain other additives as component (J). Those additives include retarders to modify the working and setting time (e.g. 3-methyl-1-butyne-3-ol or 1,1,3,3-tetramethyl-1, 3-divinyl siloxane (VMO)), inhibitors, pigments, dyes, plastizers (including paraffin oil or mineral oil), odorous substances, flavourings, or hydrogen scavenger etc. alone or in admixture.

To control the reactivity of the addition reaction and to prevent premature curing, it may be advantageous to add an inhibitor, which prevents the addition reaction for a specific period of time or slows the addition reaction down. Such inhibitors are known and described, e.g. in U.S. Pat. No. 3,933,880. This content of this reference regarding such inhibitors and their preparation is expressly regarded as being part of the disclosure of the invention and herewith incorporated by reference.

Examples of such inhibitors include acetylenic unsaturated alcohols such as 3-methyl-1-butyne-3-ol, 1-ethynylcyclo hexane-1-ol, 3,5-dimethyl-1-hexyne-3-ol and 3-methyl-1-pentyne-3-ol. Examples of inhibitors based an vinyl siloxane are 1,1,3,3-tetramethyl-1,3-divinyl siloxane, 1,3,5, 7-tetravinyl-1,3,5,7-tetramethylcyclotetrasiloxane and poly-, oligo- and disiloxanes containing vinyl groups.

The composition may also contain a component useful for diminishing the presence or degree of hydrogen outgassing which may be typically generated as a result of the vinyl polymerization in the case of SiH curable composition. The composition thus may comprise a hydrogen scavenger such as finely divided platinum metal that scavenges for and takes up such hydrogen. The Pt metal may be deposited upon a substantially insoluble salt having a surface area of between about 0.1 and about 40 m$^2$/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to about 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal (e.g. as described e.g. in U.S. Pat. No. 4,273,902) or Pd compounds (e.g. as disclosed in to U.S. Pat. No. 5,684,060) can be employed.

Component (J) can be present in the following amounts:
Lower limit: at least about 0 or at least about 0.0001 or at least about 0.001 wt.-%;
Upper limit: utmost about 60 or utmost about 30 or utmost about 10 wt.-%;
Range: from about 0 to about 60 or from about 0.0001 to about 30 or from about 0.001 to about 10 wt.-%;
wt.-% with respect to the weight of the whole composition.

According to one embodiment the dental impression composition contains the components in the following amounts:

| Component | Base paste (wt.-%) | Catalyst paste (wt.-%) | Total in base and catalyst paste (wt.-%) |
|---|---|---|---|
| (A) | 10-60 | 10-60 | 10-60 |
| (B) | 0.2-40 | — | 0.1-20 |
| (C) | — | 0.0001-0.1 | 0.00005-0.05 |
| (D) | 0.1-20 | 0-20 | 0.05-20 |

-continued

| Component | Base paste (wt.-%) | Catalyst paste (wt.-%) | Total in base and catalyst paste (wt.-%) |
|---|---|---|---|
| (E)  | 5-80 | 5-80 | 5-80 |
| (F1) | 0.0002-0.2 | — | 0.0001-0.1 |
| (F2) | 0.0002-0.2 | 0-0.1 | 0.0001-0.1 |
| (G)  | 0-20 | 0-20 | 0-20 |
| (H)  | 0-20 | 0-20 | 0-20 |
| (I)  | 0-30 | 0-30 | 0-30 |
| (J)  | 0-30 | 0-30 | 0-30 |

According to another embodiment the dental impression composition contains the components in the following amounts:

| Component | Base paste (wt.-%) | Catalyst paste (wt.-%) | Total in base and catalyst paste (wt.-%) |
|---|---|---|---|
| (A)  | 20-55 | 20-55 | 20-55 |
| (B)  | 2-30 | — | 1-15 |
| (C)  | — | 0.0001-0.1 | 0.00005-0.05 |
| (D)  | 3-10 | 0-10 | 1.5-5 |
| (E)  | 20-70 | 20-70 | 20-70 |
| (F1) | 0.0005-0.07 | — | 0.00025-0.035 |
| (F2) | 0.0005-0.07 | 0-0.7 | 0.00025-0.035 |
| (G)  | 0-15 | 0-15 | 0.2-15 |
| (H)  | 0-5 | 0-5 | 0.01-5 |
| (I)  | 0-20 | 0-20 | 0-20 |
| (J)  | 0-10 | 0-10 | 0-10 |

The amount of catalyst (C) is given in wt.-% calculated with respect to the amount of Pt contained in the catalyst component.

The dental impression composition described in the present text is typically prepared by mixing the respective components of the composition. If desired, mixing can be accomplished by using a kneading machine or a dissolver.

The dental compositions described in the present text are typically multi component materials which comprise at least a curable base paste and a catalyst paste comprising a catalyst for curing at least part of the material of the base paste.

Accordingly, the components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base paste and a catalyst paste separated from each other before use, wherein the base paste comprises components (A), (B), (D), (E) and (F) and the catalyst paste comprises component (C) or (C), (E) and (A).

The other optional components (G), (H), (I) and (J) can be present in the base paste or the catalyst paste or in the base paste and the catalyst paste.

According to another embodiment the stabilizer(s) (F) is/are present in the base paste only but not in the catalyst paste.

According to another embodiment, the hydrophilating agent(s) (D) is/are present in the base paste only but not in the catalyst paste.

According to another embodiment, component (F1) is:

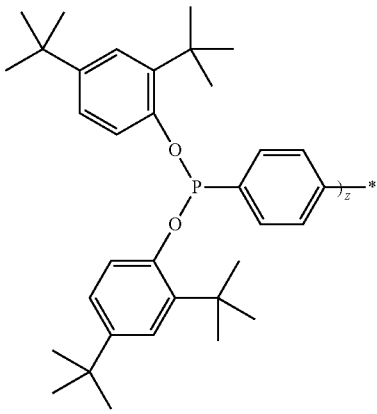

with z = 2 and component (F2) is pentaerythritoltetrakis(3-(3,5-di-tert-butyl-4-hydroxyphenyl)propionate)

According to another embodiment, the mixing ratio of the base paste to the catalyst paste is about 1:1. This may facilitate the mixing of the base and catalyst paste. According to a further embodiment, the pastes of the kit of part are contained in a cartridge made of plastic material. Using a cartridge made of plastic material can be beneficial due to its better permeability with respect to gases like oxygen and/or hydrogen compared to foil bags.

The cartridge typically has at least two compartments for separately storing each of the pastes to be mixed before use. Each compartment typically contains a movable plunger and an opening to dispense the paste into the orifice(s) of a mixing tip.

Example of such cartridges are described in EP 0 319 639 A1. The content of this reference is herewith incorporated by reference. Suitable cartridges are also commercially available e.g. from SulzerMixpac Comp.

According to another embodiment, (G) is present in the base paste only.

According to another embodiment, components (F1) and (F2) are present in equal amounts with respect to weight, The volume ratios of catalyst paste and base paste can range from about 10:1 to about 1:10. Particularly preferred volume ratios of base paste to catalyst paste are about 1:1 and about 5:1 (5 parts of base paste to 1 part of catalyst paste).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 5,924,600, U.S. Pat. No. 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as are described e.g. in U.S. Pat. No. 5,249,862, U.S. Pat. No. 5,286,105 and U.S. Pat. No. 5,332,122. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2 or Pentamix™ 3.

In practice, the impression material can be syringed through a static or mechanical mixing device into an impression tray or onto patient's teeth or tissue and placed in the patient's mouth. After the impression material is set, the tray is removed from the patient's mouth and, in instances where the dental practitioner prepares the positive model, it may be preferable to pour the positive model material immediately after removal of the impression from the patient's mouth.

The dental impression composition described in the present text is used for making dental impressions of the dental situation in the mouth of a patient. The dental impression materials can be used as precision impression materials, situation impression materials or bite registration impression materials.

The dental impression material can also be used for the production of (temporary or long term) crown and/or bridges. In the latter case, the composition is used as a mould to be filled with the (temporary or long term) crown and/or bridge material, which is typically based on polymerizable (meth)acrylates.

The method of taking a dental impression typically comprises the steps of:
providing a dental impression composition as described in the present text,
bringing the dental impression composition in contact with a tooth surface,
letting the dental impression composition set,
removing the dental impression composition from the tooth surface.

According to one embodiment, the dental impression material described in the present text has the following composition:
as component (C) a Pt containing catalyst,
as component (D) a hydrophilating agent as described above in an amount from about 0.75 to about 4 wt.-%,
as component (E) cristobalite in an amount of about 30 to about 55 wt.-%,
as component (F1) a compound selected from those described above in an amount from about 0.001 to about 0.02 wt.-%,
as component (F2) a compound being selected from antioxidants comprising a phenolic moiety in an amount from about 0.001 to about 0.02 wt.-%,
as component (G) a compound selected from those described above in an amount from about 0 to about 2.5 wt.-%,
as component (H) a compound having the formula $SiR^2_x((CH_2)-Si-((CH_2)_m-CH=CH_2)_3)_{4-x}$ in which $R^2$ is a monovalent radical without groups that can undergo an addition reaction with SiH-groups with 1 to 12 carbon atoms, n=2, 3, 4 or 5, m=0, 1, 2 or 3, and x=0 or 1 in an amount from about 0 to about 1.5 wt.-%,
wt.-% with respect to the weight of the whole composition.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Measurements
Determination of Setting Time

The setting time of the compositions was determined by measuring the viscosity in dependence on the time at 33° C. by using a MDR 2000 rheometer from Alpha instruments under aerobic conditions at 50% humidity. The setting time was determined as the t90 value, at which 90% of the final viscosity was achieved. Another characteristic size is the t5 value, at which 5% of the final viscosity was present. Until this time the composition can be assumed to be almost free of network formation (curing).

Viscosity

If desired, the viscosity can be measured at 23° C. using a Haake Rotovisco 1 device with a plate/plate system (diameter 20 mm) and a slit of 0.2 mm. The viscosity values (Pas) and share stress values (Pa) are recorded for each share rate (starting from 10 l/s to 110 l/s in 10 l/s steps. For each share rate, a delay of 5 seconds was used before collecting data. The above mentioned method of measurement corresponds essentially to DIN 53018-1.

Water Contact Angle

If desired, the water contact angle of the un-cured paste can be measured as follows: Test specimen preparation: For the preparation of test piece the mixed paste is subjected to an object slide and flattened and triturated by a second object slide in order to obtain a thin film. The test piece preparation is performed in that simplified way as the thickness of the film does not have a significant effect on the measured water contact angle (see G. Kugel, T. Klettke, J. A. Goldberg, J. Benchimol, R. D. Perry, S. Sharma, J. Prosthod. 2007, 16, 84-92). Measurement: The object slide is placed on the table of a Drop Shape Analyse System DSA 10 (Kriiss GmbH, Hamburg), a well known device for measuring contact angles. 5 μl of water are placed onto the surface of the specimen and an automatic contact angle measurement is started using standard software of the goniometer. Measuring time is at least about 10 s up to about 200 s. The water contact angle is measured at different time periods after mixing of base paste and catalyst paste, especially after 25 s. The data (video sequences) is evaluated by the "circle fitting" method, another standard method for data evaluation (see G. Kugel, T. Klettke, J. A. Goldberg, J. Benchimol, R. D. Perry, S. Sharma, J. Prosthod. 2007, 16, 84-92); $\Theta_{2s}$ is the angle obtained 2 s after placing the water drop on the surface.

Shelf Life Time Determination

For the determination of the shelf life time, the Base Pastes B and C were filled in combination with Catalyst Paste D in a conventional dual chamber cartridge (volume 1:1; Sulzer Mixpack) and stored at 50° C. After the storage time given in Table 2 below, the setting time was determined according to the method described above by mixing the stored Base and Catalyst pastes.

Materials

|  | Availability |
| --- | --- |
| Fluorinated polyether | as described in US 2004/0124396 |
| Polyether derivate | as described above |
| Unsaturated carbosilane crosslinker having a molecular weight below 500 g/mol | as described above |
| Hostanox ™ | as described above |
| Irganox ™ 1010 | as described above |
| Vinylpolydimethylsiloxan (5-7 Pa*s) | CAS: 68093-19-2 |
| Polydimethylhydrosiloxan | CAS: 68037-59-2 |

Composition I
Base Paste A was obtained by mixing the following ingredients to a homogenous paste:

| | |
|---|---|
| Vinylpolydimethylsiloxan (Comp. A) | 30-50% |
| Polydimethylhydrosiloxan (Comp. B) | 10-20% |
| Cristobalite (Comp. E) | 20-40% |
| Pyrogenic silica (Comp. E) | 1-10% |
| Allytrimethylsilan (Comp. G) | <5% |
| Fluorinated polyether (Comp. D) | 1-5% |
| Peppermint flavour (Comp. J) | <1% |
| Unsaturated carbosilane crosslinker (Comp. H) | <1% |
| Polyether derivate (Comp. D) | <1% |

The stabilizers (F1) and (F2) were dissolved (in the amounts given in Table 1) in heptamethyltrisiloxane modified with polyalkylenoxide (D) resulting in Solution 1 (S1) and Solution 2 (S2). 4 wt.-% of the respective solution of the stabilizers in the silicone surfactant were added to Base Paste A, resulting in Base Pastes B and C, respectively.

TABLE 1

| | S1 | S2 |
|---|---|---|
| Hostanox ™ (Comp. F1) | 0.4% | 0.4% |
| Irganox ™ 1010 (Comp. F2) | | 0.4% |
| Base paste | B | C |

Catalyst Paste D was obtained by mixing the following ingredients to a homogenous paste:

| | |
|---|---|
| Vinylpolydimethylsiloxan (Comp. A) | 40-60% |
| Pyrogenic silica (Comp. E) | 5-20% |
| Crystalline silica filler (Comp. E) | 20-40% |
| Peppermint flavour (Comp. J) | <1% |
| Pt-catalyst in Poly(dimethylsiloxan) (Comp. C) | 1-10% |
| Unsaturated carbosilane crosslinker (Comp. H) | <1% |
| Pigments (Comp. J) | <2% |
| Hydrogen scavanger (Comp. J) | <1% |

The respective Base Paste and Catalyst Paste were filled in a dual chamber cartridge (volume ratio 1:1; SulzerMixpac Comp.) equipped with a static mixing tip (SulzerMixpac Company). The pastes were extruded from the cartridge and mixed using a hand mixing apparatus (3M ESPE Comp.).

TABLE 2

| 50° C. | t90 | |
|---|---|---|
| Base/catalyst | B/D | C/D |
| 0 | 1.46 | 1.61 |
| 1 month | 1.77 | 1.27 |
| 2 month | 2.54 | 1.23 |
| 3 month | 2.63 | 1.23 |
| 6 month | 5.13 | 1.42 |
| 9 month | 6.91 | 1.29 |

Table 2 shows that Base Paste B shows a prolongation of the t90 value, whereas Base Paste C remains almost unchanged.

This demonstrates, that the shelf life can be improved by using a phosphorous containing stabilizer as component (F1) in combination with an antioxidants as component (F2).

Composition II
Composition II describes another example of a possible formulation of the inventive dental impression composition.

Base Paste:

| | |
|---|---|
| Mixture of vinyl terminated polydimethylsiloxane (7900 mPas) | 45.0% (weight) |
| Poly(methyl)(hydrogen)siloxane (40-160 mPas) | 11.5% (weight) |
| Pyrogenic silica (hydrophobized, 100 m2/g) | 5.0% (weight) |
| Cristobalilte filler (<20 μm) | 34.5% (weight) |
| Surfactant | 3.968% (weight) |
| Hostanox P-EPQ | 0.016% (weight) |
| Irganox 1010 | 0.016% (weight) |

Catalyst Paste:

| | |
|---|---|
| Mixture of vinyl terminated polydimethylsiloxane (5800 mPas) | 48.6% (weight) |
| Tetraallylsilane | 0.5% (weight) |
| Platin tetramethyldivinyldisiloxane complex 1.3 wt.-% Pt in silicone oil | 1.6% (weight) |
| Palladium chloride dispersion | 0.1% (weight) |
| Pyrogenic silica (hydrophobized, 100 m²/g) | 5.7% (weight) |
| Cristobalite (<20 μm) | 42.7% (weight) |
| Pigment dispersion | 0.8% (weight) |

Composition III
Base Paste E:
Base Paste E was obtained by mixing the following ingredients to a homogenous paste:

| | |
|---|---|
| Mixture of vinyl terminated polydimethylsiloxane (7900 mPas) | 47.5% (weight) |
| Poly(methyl)(hydrogen)siloxane (40-160 mPas) | 11.5% (weight) |
| Pyrogenic silica (hydrophobized, 100 m2/g) | 2.75% (weight) |
| Cristobalilte filler (<20 μm) | 35.3% (weight) |
| Surfactant | 2.98% (weight) |
| Hostanox P-EPQ | 0.012% (weight) |

Irganox 1010 0.012% (weight)
Base Paste F:
Base Paste F was obtained by mixing the following ingredients to a homogenous caste:

| | |
|---|---|
| Mixture of vinyl terminated polydimethylsiloxane (7900 mPas) | 47.5% (weight) |
| Poly(methyl)(hydrogen)siloxane (40-160 mPas) | 11.5% (weight) |
| Pyrogenic silica (hydrophobized, 100 m2/g) | 2.75% (weight) |
| Cristobalilte filler (<20 μm) | 35.3% (weight) |
| Surfactant | 2.99% (weight) |
| Hostanox P-EPQ | 0.012% (weight) |

Catalyst Paste G:
Catalyst Paste G was obtained by mixing the following ingredients to a homogenous paste:

| | |
|---|---|
| Mixture of vinyl terminated polydimethylsiloxane (5800 mPas) | 49.1% (weight) |
| Tetraallylsilane | 0.5% (weight) |
| Platin tetramethyldivinyldisiloxane complex 1.3 wt.-% Pt in silicone oil | 1.6% (weight) |
| Palladium chloride dispersion | 0.1% (weight) |
| Pyrogenic silica (hydrophobized, 100 m2/g) | 3.5% (weight) |
| Cristobalite (<20 μm) | 44.6% (weight) |
| Pigment | 0.6% (weight) |

The respective Base Paste and Catalyst Paste were filled in a dual chamber cartridge (volume ratio 1:1; SulzerMixpac Comp.) equipped with a static mixing tip (SulzerMixpac Company). The pastes were extruded from the cartridge and mixed using a hand mixing apparatus (3M ESPE Comp.).

TABLE 3

| 50° C. | t90 | |
| --- | --- | --- |
| Base/catalyst | E/G | F/G |
| 0 | 3.27 | 3.42 |
| 1 month | 2.90 | 3.49 |
| 2 month | 3.05 | 4.20 |
| 3 month | 2.87 | 5.60 |
| 6 month | 2.57 | 7.58 |

Table 3 shows that Base Paste E shows a prolongation of the t90 value, whereas Base Paste F remains almost unchanged.

This demonstrates, that the shelf life can be improved by using a phosphorous containing stabilizer as component (F1) in combination with an antioxidants as component (F2).

The invention claimed is:

1. A dental impression composition which is curable at a temperature below 50° C., comprising:
   (A) a curable organopolysiloxane polymer as component (A);
   (B) a crosslinker compound capable of crosslinking said organopolysiloxane polymer as component (B);
   (C) a catalyst as component (C) capable of catalyzing a crosslinking reaction of component (A) and component (B);
   (D) a hydrophilizing agent as component (D);
   (E) a filler as component (E) comprising cristobalite;
   (F1) a stabilizer as component (F1) selected from compounds comprising a phosphite moiety and mixtures thereof;
   (F2) a stabilizer as component (F2) selected from antioxidants and mixtures thereof;
   the composition being present in the form of a base paste and a catalyst paste physically separated from another,
   the base paste comprising components (A), (B), (D), (E), (F1), (F2), and
   the catalyst paste comprising components (A), (C), (E).

2. The composition of claim 1, stabilizer component (F2) being selected from antioxidants comprising a sterically hindered phenolic moiety and mixtures thereof.

3. The composition of claim 1, stabilizer component (F2) being selected from vitamin E; N,N'-di-2-butyl-1,4-phenylenediamine; N,N'-di-2-butyl-1,4-phenylenediamine; 2,6-di-tert-butyl-4-methylphenol; 2,4-dimethyl-6-tert-butylphenol; 2,4-dimethyl-6-tert-butylphenol; 2,6-di-tert-butyl-4-methylphenol; 2,6-di-tert-butylphenol; pentaerythritoltetrakis(3-(3,5-di-tert-butyl-4-hydroxyphenyl)propionate); octyl-3,5-Di-tert-butyl-4-hydroxy-hydrocinnamate; octadecyl 3-(3,5-di-tert-butyl-4-hydroxyphenyl) propionate; 1,3,5-trimethyl-2,4, 6-tri s(3,5-di-tert-butyl-4-hydroxybenzyl)benzene; 2,2,4,4-tetrakis-tert-butyl-3,3-dihydroxybiphenyl; 4,4-butylidenebis(6-tert-butyl-m-cresol); 4,4'-isopropyliden-bis-(2-tert-butylphenol); 2,2'-methylenebis(6-nonyl-p-cresol), 1,3,5-tri s(3,5-di-tert-butyl-4-hydroxybenzyl)-1,3,5-triazine-2,4,6(1H,3H,5H)trione; or combinations thereof.

4. The composition of claim 1, wherein the stabilizer component (F1) is a compound of the formula $R^1{}_nP(OR)_{3-n}$, n is 0, 1, 2 or 3, R and $R^1$ can independently from each other be

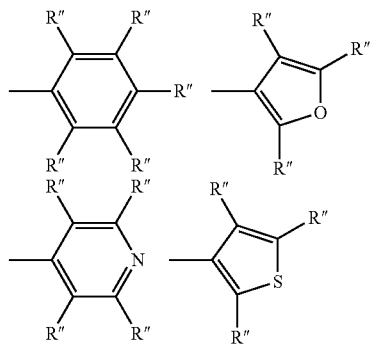

with R" independently from each other being H, $C_1$-$C_{18}$-alkyl, $C_6$-$C_{30}$-aryl or $C_7$-$C_{31}$-alkylaryl, halogen (Hal), $SiR_3$, OR or
wherein the stabilizer is a compound according to the formula

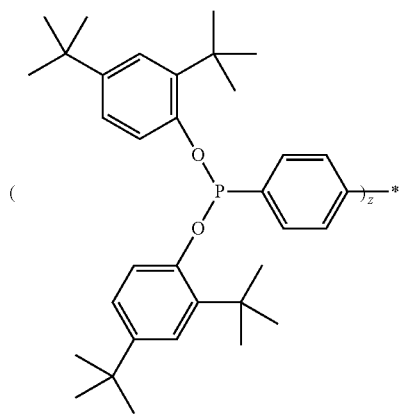

triphenylphosphite or
diisodecylphenylphosphite or
a triarylphosphite.

5. The composition of claim 1, wherein the hydrophilizing agent (D) is selected from:
   silicone moieties containing component(s) having the following formula

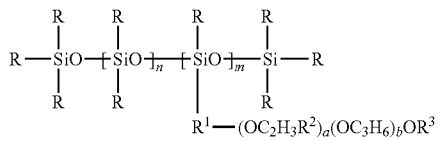

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one;
F-containing component(s) having the following formula

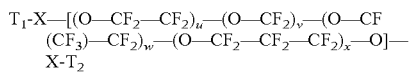

with u=0 to 8, v=0 to 8, w=0 to 14 and x=0 to 8 and u+v+w+x≥1, wherein $T_1$ and $T_2$ can be equal or different and are independently selected from the group consisting of —COOR, —$CONR^bR^c$—$CH_2OH$, —$CF_2OR$, —CHFOH, —CHFOR, —$CH_2OR$ or —F with R and being a linear or branched alkyl residue (C1 to C9), aryl residue (C1 to C9) or alkylaryl residue (C1 to C9) each of which may optionally be substituted with one or more substituents selected from the group consisting of hydroxyl, amino group, halogen atom, an SiH group and a group capable of reacting with SiH, $R^b$ and $R^c$ independently representing H or having a meaning as given for R, and wherein X is selected from $(CF_2)_{1-6}$, $CF(CF_3)$ and CHF—$CF_2$;

$R^1$—O—$[CH_2CH_2O]_n$—$[R^2O]_m$—$R^3$, wherein $R^1$ represents an aromatic or aliphatic, linear or branched hydrocarbon group having at least 8 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2, ethylene oxide or propylene oxide polymers or ethylene-propylene block polymers bearing as end groups polymerizable moieties selected from vinyl, allyl, —OCO—$(CH_3)C$=$CH_2$;

$H_3C$—CO—$[CH_2$—$CH_2$—O—$]_m$—$[CH_2$—$CH_2$—$CH_2$—O$]_n$—CO—$CH_3$ with n,m=10 to 100;

or combinations thereof.

6. The composition of claim 1, wherein the filler is characterized by at least one or all of the following features:
Mean particle size: 2-20 μm;
pH-value of a dispersion of 20 g filler in 50 ml of an aqueous $CaCl_2$ solution: about 3 to about 10.

7. The composition of claim 1, wherein the filler is present in an amount of from about 5 to about 80 wt.-%, wt.-% with respect to the weight of the whole composition.

8. The composition of claim 1, wherein the composition comprising in addition at least one of or all of the following components:
(G) silane compound with only one ethylenically unsaturated group;
(H) silane compound with at least 2 ethylenically unsaturated groups;
(I) organopolysiloxanes without unsaturated groups;
(J) additives;
being either contained in the base paste or the catalyst paste or the base paste and the catalyst paste.

9. The composition of claim 1, further comprising a silane compound as component (G) being characterized by the formula:

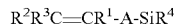

$R^1$, $R^2$, $R^3$ can be equal or different and comprise hydrogen or monovalent alkyl C1-C22, aryl C6-C12, wherein $R^1$ and $R^2$ or $R^3$ can form a cyclic structure, and wherein $R^1$, $R^2$ and $R^3$ may include O, Cl, Br, F or I, R4 can be a monovalent alkyl C1-C22, aryl C6-C12, alkoxy C1-C22, aryloxy C6-C12, O—$SiR^5_3$ or H, wherein $R^4$ may include O, Cl, Br, F or I, $R^5$ can be monovalent alkyl C1-C22, aryl C6-C12, wherein two or three of the residues $R^4$ in O—$SiR^4_3$ can combine to a cyclic or polycyclic structure, A is a divalent linear, branched or cyclic hydrocarbon group C1-C12, optionally comprising an aromatic moiety, with at least one methylene group directly attached to the unsaturation, optionally including O-Atoms.

10. The composition of claim 1, further comprising a silane compound as component (H) being characterized by the formula:
$Si(R^1)_n(R^2)_{4-n}$, wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups with 1 to 12 carbon atoms and n is 2, 3 or 4, or a silane compound of the general formula: $(R^1)_m(R^2)_{3-m}$Si-A-Si—$(R^1)_m(R^2)_{3-m}$, wherein $R^1$ and $R^2$ are independently from each other defined as above, A is a bivalent linear or branched or alicyclic, heterocyclic, aromatic or heteroaromatic group with 1 to 10000 carbon atoms which can contain nitrogen or oxygen atoms and m is 2 or 3, or a dendrimer of the following formula $SiR^2_x((CH_2)_n$—Si—$((CH_2)_m$—CH=$CH_2)_3)_{4-x}$ in which $R^2$ is defined as above, n=2, 3, 4 or 5, m=0, 1, 2 or 3, and x=0 or 1.

11. The composition of claim 1, further comprising component (J) comprising at least one or more of the following components: retarder(s), inhibitor(s), pigment(s), dye(s), plasticizer(s), odorous substance(s), flavouring(s), or hydrogen scavenger(s).

12. The composition of claim 1 comprising the components in the following amounts:
Component (A): from about 10 to about 60 wt.-%,
Component (B): from about 0.1 to about 20 wt.-%,
Component (C): from about 0.00005 to about 0.05 wt.-% calculated on the amount of Pt,
Component (D): from about 0.05 to about 20 wt.-%,
Component (E): from about 5 to about 80 wt.-%,
Component (F1): from about 0.0001 to about 0.1 wt.-%, and
Component (F2): from about 0.0001 to about 0.1 wt.-%,
wt.-% with respect to the weight of the whole composition.

13. The composition of claim 1, wherein the material comprises:
as component (C) a Pt containing catalyst;
as component (E) cristobalite in an amount of about 30 to about 55 wt.-%;
as component (F2) a compound being selected from antioxidants comprising a sterically hindered phenolic moiety in an amount from about 0.001 to about 0.02 wt.-%;
the composition further comprising:
as component (H) a compound having the formula $SiR^2_x((CH_2)_n$—Si—$((CH_2)_m$—CH=$CH_2)_3)_{4-x}$ in which $R^2$ is a monovalent radical without groups that can undergo an addition reaction with SiH-groups with 1 to 12 carbon atoms, n=2, 3, 4 or 5, m=0, 1, 2 or 3, and x=0 or 1 in an amount from about 0 to about 1.5 wt.-%;
wt.-% with respect to the weight of the whole composition.

14. Method of taking a dental impression, the method comprising;
providing a dental impression composition of claim 1;
bringing the dental impression composition in contact with a tooth surface;
letting the dental impression composition set; and
removing the dental impression composition from the tooth surface.

15. A method for increasing the shelf-life of a dental impression composition comprising cristobalite as filler, the method comprising:
   providing a dental impression composition according to claim 1, wherein the combination of stabilizer components (F1) and (F2) increases the shelf-life of the dental impression composition.

16. The composition of claim 5, wherein component (D) is present in an amount from about 0.75 to about 4 wt.-%.

17. The composition of claim 4, wherein component (F1) is present in an amount from about 0.001 to about 0.02 wt.-%.

18. The composition of claim 9, wherein component (G) is present in an amount from about 0 to about 2.5 wt.-%.

* * * * *

UNITED STATES PATENT AND TRADEMARK OFFICE
CERTIFICATE OF CORRECTION

PATENT NO. : 9,549,881 B2
APPLICATION NO. : 14/767167
DATED : January 24, 2017
INVENTOR(S) : Peter Osswald It is certified that error appears in the above-identified patent and that said Letters Patent is hereby corrected as shown below:

In the Specification

Column 1
Line 20, delete "azridino" and insert -- aziridino --, therefor.

Column 2
Line 60, delete "unsaturred" and insert -- unsaturated --, therefor.

Column 2
Line 66, delete "the" and insert -- The --, therefor.

Column 4
Line 7, delete "iso-proply" and insert -- iso-propyl --, therefor.

Column 4
Line 7, delete "ter.-butyl)" and insert -- tert-butyl) --, therefor.

Column 7
Line 67, delete "unsatured" and insert -- unsaturated --, therefor.

Column 13
Line 14, delete "H$_4$ O)y" and insert -- H$_4$O)y --, therefor.

Column 13
Line 22, delete "CH$_2$CH$_2$" and insert -- CH$_2$—CH$_2$ --, therefor.

Column 13
Line 24, delete "CH$_2$CH$_2$" and insert -- CH$_2$—CH$_2$ --, therefor.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)

Column 13
Line 26, delete "CH$_3$," and insert -- CH$_3$; --, therefor.

Column 13
Line 36, delete "p 4," and insert -- p. 4, --, therefor.

Column 13
Line 59, delete "oxethylates" and insert -- oxyethylates --, therefor.

Column 14
Line 22, delete "]$_m$[" and insert -- ]$_m$-[ --, therefor.

Column 14
Line 29, delete "CF$_2$)$_n$—" and insert -- CF$_2$)$_u$— --, therefor.

Column 14
Line 34, delete "—CONR$_b$R$_c$" and insert -- —CONR$^b$R$^c$, --, therefor.

Column 14
Line 41, delete "R$_b$" and insert -- R$^b$ --, therefor.

Column 14
Line 53, after "atoms" insert -- , --.

Column 14
Line 56, after "residue" delete "rest".

Column 15
Line 2, delete "hexafluoropropylenoxide," and insert -- hexafluoropropylene oxide, --, therefor.

Column 15
Line 7, delete "—CONR$_b$R$_c$," and insert -- —CONR$^b$R$^c$, --, therefor.

Column 15
Line 10, after "residue" delete "rest".

Column 15
Line 14, delete "Rb" and insert -- R$^b$ --, therefor.

Column 15
Line 14, delete "Rc" and insert -- R$^c$ --, therefor.

Column 15
Lines 18-19, delete "hexafluoropropylenoxide" and insert -- hexafluoropropylene oxide --, therefor.

Column 15
Line 21, delete "hexafluoropropylenoxide," and insert -- hexafluoropropylene oxide, --, therefor.

Column 17
Line 29, delete "(OCF(CF$_3$)CF$_2$) (OCF$_2$)$_m$" and insert -- (O—CF(CF$_3$)—CF$_2$)$_n$—(O—CF$_2$)$_m$ --, therefor.

Column 17
Line 37, delete "—CONR$_b$R$_c$," and insert -- —CONR$^b$R$^c$, --, therefor.

Column 17
Line 44, delete "R$_b$" and insert -- R$^b$ --, therefor.

Column 17
Lines 59-60, delete "hydrophiliating" and insert -- hydrophilating --, therefor.

Column 18
Line 1, delete "CF$_2$O]" and insert -- CF$_2$O]$_n$ --, therefor.

Column 18
Line 14, delete "hydrophiliating" and insert -- hydrophilating --, therefor.

Column 18
Line 16, delete "hydrophiliating" and insert -- hydrophilating --, therefor.

Column 20
Line 4, delete "organophosphorous" and insert -- organophosphorus --, therefor.

Column 20
Line 6, delete "R═C$_1$" and insert -- R=C$_1$ --, therefor.

Column 20
Line 7, delete "R$^1$═R" and insert -- R$^1$=R --, therefor.

Column 20
Line 7, delete "H═R" and insert -- H=R --, therefor.

Column 20
Line 10 (approx.), delete "R═C$_1$" and insert -- R=C$_1$ --, therefor.

Column 20
Line 11 (approx.), delete "R$^1$═C$_1$" and insert -- R$^1$=C$_1$ --, therefor.

Column 22
Line 2, delete "p henylene diamine;" and insert -- phenylenediamine; --, therefor.

Column 22
Line 3, delete "phenylene diamine;" and insert -- phenylenediamine; --, therefor.

Column 22
Line 17 (approx.), after "thereof" insert -- . --.

Column 22
Line 59, delete "unsatured" and insert -- unsaturated --, therefor.

Column 23
Line 1, delete "and or" and insert -- and/or --, therefor.

Column 23
Line 56, delete "Decycl," and insert -- Decyl, --, therefor.

Column 23
Line 62, delete "octasiloxan-1-yl)," and insert -- octasiloxan-1-yl). --, therefor.

Column 24
Line 6, delete "decyclene)." and insert -- decylene). --, therefor.

Column 24
Line 28, delete "3 Si" and insert -- 3Si --, therefor.

Column 24
Line 30, delete "8 Si" and insert -- 8Si --, therefor.

Column 24
Line 34, delete "3;H2C" and insert -- 3; H2C --, therefor.

Column 24
Line 52, delete "3 Si" and insert -- 3Si --, therefor.

Column 25
Line 18, delete "$Si(R^1)_n(R^2)_{4-n}.$" and insert -- $Si(R^1)_n(R^2)_{4-n}$ --, therefor.

Column 25
Line 35, delete "$(R^1)_m(R^2)_{3-m}Si-A-Si-(R^1)(R^2)_3,$" and insert -- $(R^1)_m(R^2)_{3-m}Si-A-Si-(R^1)_n(R^2)_{3-n}$ --, therefor.

Column 25
Line 47, delete "penylene," and insert -- pentalene, --, therefor.

Column 26
Line 20 (approx.), delete "$SiR^2_x((CH_2)_n-Si-((CH_2)_m-CH=CH_2)_3)_{4-n}.$" and insert -- $SiR^2_x((CH_2)_n-Si-((CH_2)_m-CH=CH_2)_3)_{4-x}$ --, therefor.

Column 26
Line 25, delete "CH$_z$" and insert -- CH$_2$ --, therefor.

Column 26
Line 64, delete "tetrallylester," and insert -- tetraallylester, --, therefor.

Column 27
Lines 29-30, delete "triazintrione" and insert -- triazinetrione --, therefor.

Column 28
Line 1, delete "plastizers" and insert -- plasticizers --, therefor.

Column 28
Lines 15-16 (approx.), delete "ethynylcyclo hexane" and insert -- ethynylcyclohexane --, therefor.

Column 28
Line 17 (approx.), delete "an" and insert -- on --, therefor.

Column 30
Line 22 (approx.), after "propionate)" insert -- . --.

Column 30
Line 43, delete "weight," and insert -- weight. --, therefor.

Column 31
Line 53, delete "SiR$^2_x$((CH$_2$)—Si" and insert -- SiR$^2_x$((CH$_2$)$_n$—Si --, therefor.

Column 32
Line 50 (approx.), delete "Mixpack)" and insert -- Mixpac) --, therefor.

Column 32
Line 64 (approx.), delete "Vinylpolydimethylsiloxan" and insert -- Vinylpolydimethylsiloxane --, therefor.

Column 32
Line 65 (approx.), delete "Polydimethylhydrosiloxan" and insert -- Polydimethylhydrosiloxane --, therefor.

Column 33
Line 6 (approx.), delete "Vinylpolydimethylsiloxan" and insert -- Vinylpolydimethylsiloxane --, therefor.

Column 33
Line 7 (approx.), delete "Polydimethylhydrosiloxan" and insert -- Polydimethylhydrosiloxane --, therefor.

Column 33
Line 9 (approx.), delete "Allytrimethylsilan" and insert -- Allyltrimethylsilane --, therefor.

Column 33
Line 33 (approx.), delete "Vinylpolydimethylsiloxan" and insert -- Vinylpolydimethylsiloxane --, therefor.

Column 33
Line 37 (approx.), delete "(dimethylsiloxan)" and insert -- (dimethylsiloxane) --, therefor.

Column 33
Line 39 (approx.), delete "scavanger" and insert -- scavenger --, therefor.

Column 34
Line 8 (approx.), delete "Cristobalilte" and insert -- Cristobalite --, therefor.

Column 34
Line 33 (approx.), delete "Cristobalilte" and insert -- Cristobalite --, therefor.

Column 34
Line 39 (approx.), delete "caste:" and insert -- paste: --, therefor.

Column 34
Line 46 (approx.), delete "Cristobalilte" and insert -- Cristobalite --, therefor.

In the Claims

Column 35
Line 57 (approx.), in Claim 3, delete "4, 6-tri s" and insert -- 4,6-tris --, therefor.

Column 35
Line 58 (approx.), in Claim 3, delete "2,2,4,4" and insert -- 2,2',4,4' --, therefor.

Column 35
Line 58 (approx.), in Claim 3, delete "3,3" and insert -- 3,3' --, therefor.

Column 35
Line 61 (approx.), in Claim 3, delete "tri s" and insert -- tris --, therefor.

Column 36
Line 39 (approx.), in Claim 4, above "triphenylphosphite or" insert -- with z=2 or --.

Column 37
Lines 42-43, in Claim 8, delete "unsatured" and insert -- unsaturated --, therefor.

CERTIFICATE OF CORRECTION (continued)
U.S. Pat. No. 9,549,881 B2

Column 38
Line 27, in Claim 11, delete "plastizer(s)," and insert -- plasticizer(s), --, therefor.

Column 38
Line 48, in Claim 13, delete "stericallly" and insert -- sterically --, therefor.